United States Patent [19]

Saupe et al.

[11] Patent Number: 5,076,831
[45] Date of Patent: Dec. 31, 1991

[54] 1,8-NAPTHALENEDICARBOXIMIDES AS ANTIDOTES

[75] Inventors: Thomas Saupe, Sandhausen; Norbert Meyer, Ladenburg; Peter Plath, Frankenthal; Ulrich Schirmer, Heidelberg; Bruno Wuerzer, Otterstadt; Karl-Otto Westphalen, Speyer; Manfred Patsch, Wachenheim; Juergen Pfister, Speyer, all of Fed. Rep. of Germany

[73] Assignee: BASF Aktiengesellschaft, Ludwigshafen, Fed. Rep. of Germany

[21] Appl. No.: 615,865

[22] Filed: Nov. 20, 1990

[30] Foreign Application Priority Data

Nov. 29, 1989 [DE] Fed. Rep. of Germany ....... 3939379
Jul. 7, 1990 [DE] Fed. Rep. of Germany ....... 4021654

[51] Int. Cl.$^5$ .................... A01N 43/02; A01N 43/40; C07D 47/06
[52] U.S. Cl. .......................................... 71/90; 71/99; 546/70; 546/99
[58] Field of Search ................... 546/99, 70; 71/94, 90

[56] References Cited

U.S. PATENT DOCUMENTS

| 4,204,063 | 5/1980 | Brana et al. | 546/99 |
|---|---|---|---|
| 4,220,777 | 9/1980 | Karg et al. | 546/98 |
| 4,254,108 | 3/1981 | Sestanj | 424/178 |
| 4,665,071 | 5/1987 | Zee-Cheng et al. | 546/99 |
| 4,892,950 | 1/1990 | Schütze et al. | 546/98 |

FOREIGN PATENT DOCUMENTS

| 2521139 | 8/1983 | France . |
|---|---|---|
| 7002672 | 1/1970 | Japan . |
| 7338212 | 12/1970 | Japan . |
| 7227777 | 7/1972 | Japan . |
| 7337738 | 11/1973 | Japan . |
| 54067035 | 11/1977 | Japan . |
| 7314760 | 5/1974 | Netherlands . |

OTHER PUBLICATIONS

Becker et al., CA80-70543e (1974).
Sawaki et al., CA82-170218n (1975).
Troesken et al., CA84-116948d (1976).
Handte et al., CA88-190816h (1978).
Ura et al., CA94-103421h (1981).
Warner et al., CA100-102943k (1984).
Conway et al., CA102-132027y (1985).
Jahn et al., CA103-215326s (1985).
Keil et al., CA103-104701r (1985).
Keil et al., CA105-23996e (1986).
Keil et al., CA105-20521k (1986).
Mazzocchi et al., *Tetrahedron Letters* 29 (5), 513–516 (1988).
*Probl. Endokrinol,* 26, 68–73, 96 (1980).
Kador et al., *Enzymology and Molecular Biology of Carbonyl Metabolism,* 353–365 (1987).
Ares et al., *J. Med. Chem.* 29 (11), 2384–2389 (1986).
El-Naggar, *Egypt, J. Chem.* 24, 127–130 (1981).
Pai et al., *Indian Journal of Chemistry* 21B, 607–611 (1982).
El-Naggar et al., *Egypt J. Chem.* 25, 445–450 (1982).
Matzios et al., *Pestic. Sci.* 17, 25–32 (1986).

Primary Examiner—Cecilia Shen
Attorney, Agent, or Firm—Keil & Weinkauf

[57] ABSTRACT

Substituted 1,8-naphthalenedicarboximides of the formula:

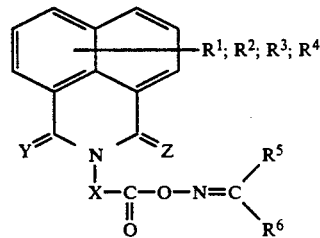

wherein $R^1$, $R^2$, $R^3$, $R^4$, $R^5$, $R^6$, X, Y, and Z have the meanings recited in the disclosure are disclosed as new compounds suitable for use as antidotes in herbicidal compositions.

9 Claims, No Drawings

1,8-NAPTHALENEDICARBOXIMIDES AS ANTIDOTES

The present invention relates to novel substituted 1,8-naphthalenedicarboximides of the general formula Ia

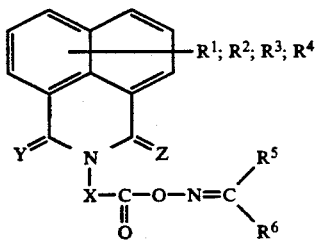

where
$R^1$ to $R^4$ are each hydrogen, halogen, hydroxyl, mercapto cyano, thiocyanato, nitro, $C_1$–$C_6$-alkyl which may be unsubstituted or partially or completely halogenated, $C_2$–$C_6$-alkenyl, $C_2$–$C_6$-alkynyl, $C_3$–$C_8$-cycloalkyl, $C_3$–$C_8$-cycloalkoxy, amino, $C_1$–$C_8$-alkylamino, di-($C_1$–$C_6$-alkylamino), amino-$C_1$–$C_4$-alkyl, $C_1$–$C_6$-alkylamino-$C_1$–$C_4$-alkyl, di-$C_1$–$C_6$-alkylamino-$C_1$–$C_4$-alkyl, $C_1$–$C_4$-alkoxy, $C_1$–$C_4$-alkylthio, $C_1$–$C_4$-alkoxy-$C_1$–$C_4$-alkyl, $C_1$–$C_4$-alkylthio-$C_1$–$C_4$-alkyl, $C_1$–$C_6$-alkylcarbonyl, $C_1$–$C_6$-alkylcarbonyloxy, $C_1$–$C_6$-alkoxycarbonyl, hydroxycarbonyl, hydroxycarbonyl-$C_1$–$C_4$-alkyl, hydroxycarbonyl-$C_1$–$C_4$-alkoxy, hydroxycarbonyl-$C_1$–$C_4$-alkylthio, hydroxysulfonyl, $C_1$–$C_6$-alkylsulfinyl, $C_1$–$C_6$-alkylsulfonyl, $C_1$–$C_4$-alkoxysulfonyl, aminosulfonyl, $C_1$–$C_4$-alkylaminosulfonyl, di-$C_1$–$C_4$-alkylaminosulfonyl, hydrazino which may carry not more than three $C_1$–$C_4$-alkyl radicals, phenyl, phenyl-$C_1$–$C_3$-alkyl, naphthyl, naphthyl-$C_1$–$C_3$-alkyl, a 5-membered or 6-membered hetaryl or hetaryl-$C_1$–$C_3$-alkyl group, phenoxy, naphthyloxy, phenylthio, naphthylthio, phenoxycarbonyl, naphthyloxycarbonyl, phenylcarbonyl, naphthylcarbonyl, phenylcarbonyloxy, naphthylcarbonyloxy, phenyl-$C_1$–$C_3$-alkoxy, naphthyl-$C_1$–$C_3$-alkoxy, a 5-membered or 6-membered hetaryl-$C_1$–$C_3$-alkoxy group, phenylsulfinyl, naphthylsulfinyl, a 5-membered or 6-membered hetarylsulfinyl group, phenylsulfonyl, naphthylsulfonyl, a 5-membered or 6-membered hetarylsulfonyl group, phenoxysulfonyl, naphthyloxysulfonyl, a 5-membered or 6-membered hetaryloxysulfonyl group, where the aryl or hetaryl moieties of the stated substituents may furthermore carry not more than three of the following substituents: halogen, cyano, nitro, $C_1$–$C_4$-alkyl, $C_1$–$C_4$-alkoxy, amino, $C_1$–$C_6$-alkylamino, di-$C_1$–$C_6$-alkylamino or partially or completely halogenated $C_1$–$C_6$-alkyl;

X is a $C_1$–$C_6$-alkylene chain which may furthermore carry one of the following radicals: halogen, hydroxyl, mercapto, $C_1$–$C_4$-alkyl, $C_1$–$C_4$-alkoxy, $C_1$–$C_4$-alkylthio, di-$C_1$–$C_4$-alkylamino, $C_1$–$C_4$-alkoxycarbonyl, cyano, $C_1$–$C_6$-alkylcarbonyl, $C_1$–$C_6$-alkylcarbonyloxy, phenyl, naphthyl, 5-membered or 6-membered hetaryl, phenyl-$C_1$–$C_3$-alkyl, naphthyl-$C_1$–$C_3$-alkyl or 5-membered or 6-membered hetaryl-$C_1$–$C_3$-alkyl, where the aryl and hetaryl moieties of the six last-mentioned radicals may furthermore carry not more than 3 halogen atoms or $C_1$–$C_4$-alkyl groups;

$R^5$ is hydrogen, cyano, $C_1$–$C_6$-alkyl, $C_2$–$C_6$-alkenyl, $C_1$–$C_4$-alkoxy-$C_1$–$C_4$-alkyl, $C_1$–$C_4$-alkylthio-$C_1$–$C_4$-alkyl, $C_1$–$C_4$-alkoxycarbonyl, acetyl, $C_3$–$C_6$-cycloalkyl, benzoyl, naphthoyl, a 5-membered or 6-membered hetaroyl group, phenyl, naphthyl, phenyl-$C_1$–$C_3$-alkyl, naphthyl-$C_1$–$C_3$-alkyl or a 5-membered or a 6-membered hetaryl or hetaryl-$C_1$–$C_3$-alkyl group, where the aryl and hetaryl moieties of the six last-mentioned groups may furthermore carry not more than three of the following radicals: halogen, hydroxyl, cyano, trifluoromethyl, $C_1$–$C_6$-alkoxy which may be unsubstituted or partially or completely halogenated, $C_1$–$C_6$-alkylthio, $C_1$–$C_6$-alkyl, di-$C_1$–$C_3$-alkylamino or acetylamino;

$R^6$ is hydrogen, cyano, $C_1$–$C_6$-alkyl which may be unsubstituted or partially or completely halogenated, $C_1$–$C_4$-alkoxy, $C_1$–$C_4$-alkoxy-$C_1$–$C_4$-alkyl, diazolylmethyl, triazolylmethyl, $C_1$–$C_6$-alkoxycarbonyl, furyl, tetrahydrofuryl, thienyl, dihydropyranyl, dihydrothiopyranyl, tetrahydropyranyl or tetrahydrothiopyranyl or phenyl when $R^5$ is hydrogen, methyl or acetyl, or together with $R^5$ and the common carbon atom, may form a $C_3$–$C_{12}$-cycloalkyl or 4-oxocyclohexadienyl radical or a 5-membered or 6-membered ring which may be saturated or partially or completely unsaturated, may contain an oxygen or sulfur atom as a hetero atom and may furthermore carry not more than three $C_1$–$C_3$-alkyl groups or a fused-on benzene ring, and Y and Z are each oxygen or sulfur, with the proviso that $R^5$ and $R^6$ are not simultaneously hydrogen, and the plant-tolerated salts of the compounds Ia in which $R^1$, $R^2$, $R^3$ and $R^4$ are each hydroxycarbonyl, hydroxycarbonyl-$C_1$–$C_4$-alkyl, hydroxycarbonyl-$C_1$–$C_4$-alkoxy, hydroxycarbonyl-$C_1$–$C_4$-alkylthio or hydroxysulfonyl.

The present invention furthermore relates to a process for the preparation of the compounds Ia and to herbicides which contain, as herbicidal active ingredients, the 2-(4-hetaryloxy)- or 2-(4-aryloxy)-phenoxyacetic acid or -propionic acid derivatives and/or cyclohexenone derivatives and, as antidotes, substituted 1,8-naphthalenedicarboximides of the formulae Ia, Ib and/or Ic and the plant-tolerated salts of compounds Ia, Ib and/or Ic in which $R^1$, $R^2$, $R^3$ and $R^4$ are each hydroxycarbonyl, hydroxycarbonyl-$C_1$–$C_4$-alkyl, hydroxycarbonyl-$C_1$–$C_4$-alkoxy, hydroxycarbonyl-$C_1$–$C_4$-alkylthio or hydroxysulfonyl and/or $R^7$ is hydroxycarbonyl-$C_1$–$C_6$-alkyl, hydroxycarbonyl-$C_1$–$C_6$-alkoxy or hydroxysulfonyl-$C_1$–$C_6$-alkyl.

The present invention also relates to methods for selectively controlling undesirable plant growth with these herbicides.

1,8-Naphthalenedicarboximides which may carry, inter alia, a group —$(CH_2)_n$—CO—N< (where n is an integer) on the imide nitrogen form the subject of JP-A 7337738-R (as whiteners) and of NL-A 7314760 (as polyamide dyes). Compounds Ib which carry a —$(CH_2)_n$—CO—O—H or —$(CH_2)_n$—CO—O-alkyl group on the nitrogen atom are described in the literature as medical active compounds or as bleaches for polymers (eg. U.S. Pat. No. 4,254,108, JP-A 54 067 035, JP-A 7338 212-R, JP-A 7227 777-R and JP-A 7002 672-R).

DE-A 27 53 152 discloses 1,8-naphthalenecarboximides which carry an unsubstituted or substituted cyanomethyl or carboxymethyl group or an acetylated carboxymethyl group on the imide nitrogen, as optical brighteners.

Herbicidal active ingredients from the group consisting of the 2-(4-hetaryloxy)- or 2-(4-aryloxy)-phenoxyacetic acid derivatives of the formula IV

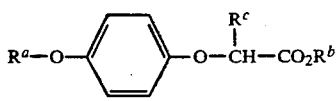

where $R^a$ is phenyl, pyridyl, benzoxazyl, benzothiazolyl or benzopyrazinyl, where these aromatic ring systems may carry not more than two of the following radicals: hydrogen, nitro, $C_1$–$C_4$-alkyl, $C_1$–$C_4$-haloalkyl and/or $C_1$–$C_4$-haloalkoxy, $R^b$ is hydrogen, $C_1$–$C_4$-alkyl or one equivalent of a plant-tolerated cation and $R^c$ is hydrogen or methyl, are disclosed in the literature, for example in DE-A-22 3 894, DE-A-24 33 067, DE-A-25 76 251, DE-A-30 04 770, BE-A-868 875 and BE-A TM 858 618.

They are used for controlling undesirable plants from the Gramineae family. However, the toleration of these substances by crops varies from commercially acceptable to non-tolerated depending on the substituents and application rate.

The same behavior is shown by cyclohexenone derivatives of the formula V

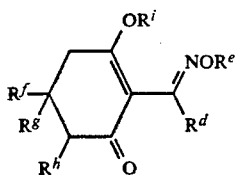

where $R^d$ is $C_1$–$C_4$-alkyl;

$R^e$ is $C_1$–$C_4$-alkyl, $C_3$- or $C_4$-alkenyl, $C_3$- or $C_4$-alkynyl or $C_3$- or $C_4$-haloalkenyl;

$C_1$–$C_4$-alkylphenyl or $C_1$–$C_4$-alken-ylphenyl, where the alkyl and alkenyl moieties may carry not more than 3 $C_1$–$C_3$-alkyl groups and/or halogen atoms and the phenyl moiety may carry not more than 5 halogen atoms or a benzyloxycarbonyl or phenyl radical and/or not more than 3 of the following substituents: nitro, cyano, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl or $C_1$–$C_4$-alkoxycarbonyl;

thienyl which may furthermore carry a halogen atom;

$R^f$ is $C_1$–$C_4$-alkyl which may be monosubstituted or disubstituted by $C_1$–$C_4$-alkylthio or $C_1$–$C_4$-alkoxy;

a 5-membered or 6-membered saturated or monounsaturated ring system which, in addition to carbon members, may contain an oxygen or sulfur atom or a sulfoxyl or sulfonyl group and in which this ring may carry not more than three of the following radicals: hydroxyl, halogen, $C_1$–$C_4$-alkyl, $C_1$–$C_4$-haloalkyl, $C_1$–$C_4$-alkoxy and/or $C_1$–$C_4$-alkylthio;

a 10-membered saturated or monounsaturated heterocyclic structure which contains two non-adjacent oxygen atoms or sulfur atoms and may be substituted by not more than three $C_1$–$C_4$-alkyl groups and/or methoxy groups;

phenyl, pyridyl, thiazolyl, pyrazolyl, pyrrolyl or isoxazolyl, where these groups may carry not more than three of the following groups: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and/or benzoylamino;

$R^g$ is hydrogen, hydroxyl or, when $R^f$ is $C_1$–$C_6$-alkyl, $C_1$–$C_6$-alkyl, $R^h$ is hydrogen, cyano, halogen, $C_1$–$C_4$-alkoxycarbonyl or a $C_1$–$C_4$-alkylketoxime group and $R^i$ is hydrogen or one equivalent of an environmentally compatible cation.

They are likewise described in the literature (eg. EP-A 228 598, EP-A 230 235, EP-A 238 021, U.S. Pat. No. 4,432,786 and DE-A 24 39 104) as herbicides and are used predominantly for controlling undesirable grasses in dicotyledon crops and in grasses which do not belong to the Gramineae family. Depending on the structure of the substituents and the dose used, compounds from this group may also be employed for selectively controlling undesirable grasses in gramineous crops, such as wheat and rice.

Cyclohexenone derivatives of the formula V in which $R^e$ is an unsubstituted or substituted alkyl or alkenyl, eg. butyl or butenylphenyl, radical, can be prepared in a conventional manner from known derivatives of the formula VIII (EP-A-80 301, EP-A-125 094, EP-A-142 741, US-A-4 249 937, EP-A-137 174 and EP-A-177 913) and the corresponding hydroxylamines of the formula IX (Houben-Weyl, 10/1, page 1181 et seq.) (EP-A-169 521).

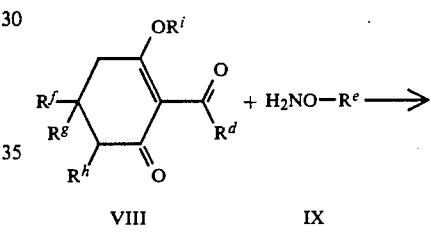

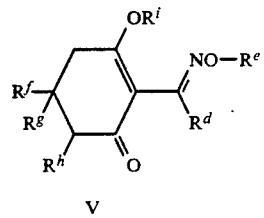

Advantageously, the reaction is carried out in the heterogeneous phase in a solvent at an adequate temperature below about 80° C. in the presence of a base, and the hydroxylamine IX is used in the form of its ammonium salt.

Examples of suitable bases are carbonates, bicarbonates, acetates, alcoholates or oxides of alkali metals or alkaline earth metals, in particular sodium hydroxide, potassium hydroxide, magnesium oxide or calcium oxide. Organic bases, such as pyridine or tertiary amines, can also be used. The base is added, for example, in an amount of from 0.5 to 2 mole equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The desired compound can be isolated, for example, by evaporating down the mixture, distributing the residue in methylene chloride/water and distilling off the solvent under reduced pressure.

However, the free hydroxylamine base, for example in the form of an aqueous solution, can also be used directly for this reaction; depending on the solvent used for the compound VIII, a single-phase or two-phase reaction mixture is obtained.

Examples of suitable solvents for this variant are alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds V can be obtained by treating the 3-hydroxy compounds with sodium hydroxide, potassium hydroxide or a sodium or potassium alcoholate in aqueous solution or in an organic solvent, such as methanol, ethanol, acetone and toluene.

Other metal salts, such as manganese, copper, zinc, iron, calcium, magnesium and barium salts, can be prepared from the sodium salts in a conventional manner, as can ammonium and phosphonium salts using ammonia or ammonium, phosphonium, sulfonium or sulfoxonium hydroxides.

Compounds of the type VIII can be prepared, for from the corresponding cyclohexane-1,3-diones of the formula X

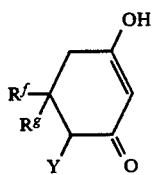  X where Y is hydrogen or methoxycarbonyl and R$^g$ is hydrogen, by known methods (Tetrahedron Lett. (1975), 2491).

It is also possible to prepare the compounds of the formula VIII via the enol ester intermediate, which is obtained in the reaction of compounds of the formula X with acyl chlorides in the presence of a base and then undergoes a rearrangement reaction with certain imidazole or pyridine derivatives (Japanese Preliminary Published Application 79/063 052).

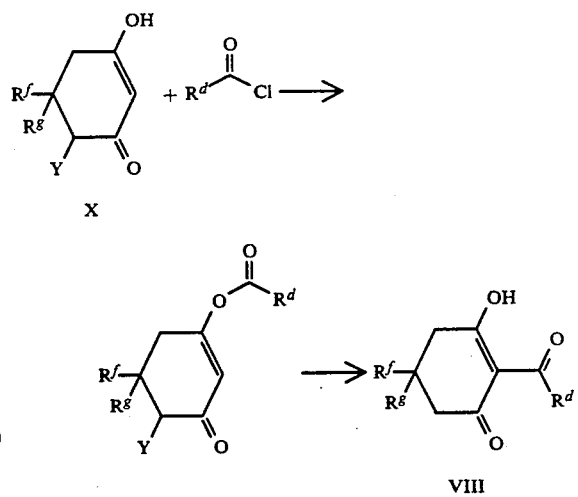

VIII

The compounds of the formula X are obtained via a number of known process steps, starting from known intermediates.

The synthesis of the hydroxylamines IX in which R$^\ominus$ is unsubstituted or substituted phenylbutyl, is carried out according to the reaction scheme below, for example via A) alkylation of cyclic hydroximides XI with suitable phenylbutyl halides and subsequent elimination of the protective group, for example with hydrazine or ethanolamine, similarly to Examples from EP-A-244 786 or Houben-Weyl, Methoden der organischen Chemie, Volume X/1, page 1152 et seq.
or B) hydrogenation of N-4-phenylbutenyloxyphthalimides, whose preparation is described in DE-A 38 38 310, by means of suitable catalysts, eg palladium on active carbon, in suitable inert solvents, such as methanol, tetrahydrofuran, dioxane, and subsequent elimination of the protective group as described above.

The hydrogenation is advantageously carried out at from 20° C. to the boiling point of the solvent, in particular at room temperature, by a conventional method, under atmospheric, superatmospheric or reduced pressure A pressure range of from 1 to 10, in particular from 1 to 2, bar is preferred Reaction scheme:

Route A)

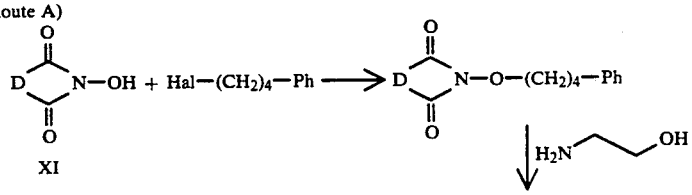

Reaction scheme:

Route B)

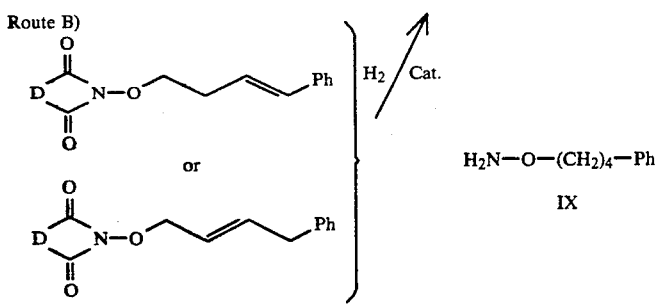

Ph = unsubstituted or substituted phenyl
Examples of suitable cyclic hydroximides XI are the following substances:

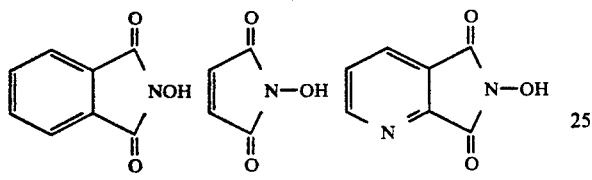

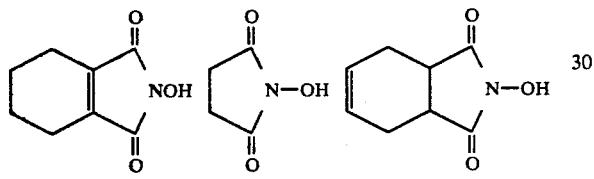

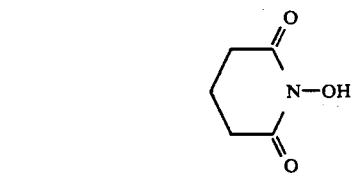

The synthesis of the hydroxylamines IX in which $R^{\ominus}$ is unsubstituted or substituted butenylphenyl and the phenyl radicals abbreviated to Ph below may in turn be unsubstituted or substituted, is carried out according to the following reaction scheme, starting from aniline derivatives, by diazotization and subsequent coupling of the diazonium salt with a correspondingly substituted butadiene XII. The resulting mixture of XIIIa and XIIIb is coupled with a cyclic hydroximide XI, and the resulting protected hydroxylamine derivative XIV is cleaved with 2-aminoethanol to give the free hydroxylamine IX:

Route C)

$$Ph-NH_2 \xrightarrow[2) CH_2=CR^i-CR^k=CHR^l]{1) \text{Diazotization/Hal}^{\oplus}}$$

$$Ph-CH_2-CR^j=CR^k-CHR^l-Hal +$$

XIIIa

$\longrightarrow$ XIIIa/XIIIb +

XIIIb

-continued

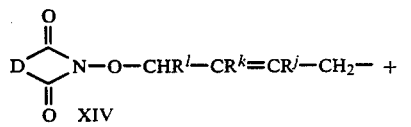

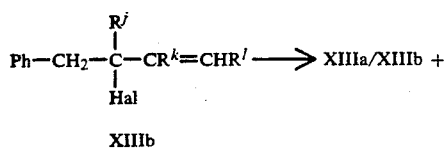

$R^j$, $R^k$ and $R^l$ independently of one another are each hydrogen, $C_1$-$C_3$-alkyl and/or halogen Hal is a halogen atom, preferably chlorine The halides XIIIa required for the above synthesis of the hydroxylamines of the formula IX can be prepared, as a mixture with XIIIb, by processes known from the literature, for example by reacting diazonium salts of aromatic and heteroaromatic anilines with dienes. The range of applications of the reaction is discussed in Organic Reactions 11 (1960), 189 or 24 (1976), 225.

Coupling of the isomeric halides XIIIa and XIIIb with a cyclic hydroxyimide of the formula XI gives exclusively the cyclic imide ethers of the formula XIV, which give the hydroxylamines IX after elimination of the protective group on the nitrogen.

The reaction with a hydroximide XI (Routes A and C) is carried out in the presence of an acid acceptor and of a solvent. For cost reasons, hydroxyphthalimide is preferably used as the hydroximide XI.

Suitable acid acceptors are alkali metal carbonates, such as potassium carbonate or sodium carbonate, alkali metal bicarbonates, such as potassium bicarbonate or sodium bicarbonate, tertiary amines, such as trimethylamine or triethylamine, and basic heterocycles, such as pyridine. For cost reasons, potassium carbonate and sodium carbonate are preferred.

Suitable solvents are aprotic dipolar organic solvents, eg. dimethylformamide, dimethyl sulfoxide and/or sulfolane.

Alkylation under phase transfer conditions is also possible. The organic solvents used here are water-immiscible compounds, such as hydrocarbons or chlorohydrocarbons. Suitable phase transfer catalysts are quaternary ammonium and phosphonium salts.

The cleavage of the cyclic imide ethers XIV is carried out similarly to a process described in EP-A-244

786, using alkanolamines. After this process, the hydroxylamines IX can be isolated as free bases or, after precipitation with acids, as salts. Readily crystallizing salts are obtained by a reaction of the bases with oxalic acid.

It is an object of the present invention to provide compounds which reduce the disadvantages encountered when the abovementioned herbicides of the formulae IV and V are used, at least to such an extent that the yield of the crops is not significantly reduced, if at all.

We have found that this object is achieeed by the substituted 1,8-naphthalenedicarboximides Ia, Ib and Ic defined at the outset.

We have furthermore found processes for the preparation of the compounds Ia and methods for the combined treatment of crops with the antidote compounds Ia and/or Ib and/or Ic on the one hand and the herbicides IV and/or V on the other hand, it being unimportant whether the herbicidal active ingredient and the antidote compound are formulated and applied together or separately or, in the case of separate application, the order in which the herbicidal active ingredient and the antidote are applied being unimportant.

Derivatives Ia, Ib and Ic having acidic terminal groups may be in the form of their agriculturally useful salts. The alkali metal salts, in particular the potassium or sodium salt, alkaline earth metal salts, in particular the calcium, magnesium or barium salt, manganese, copper, zinc and iron salts and ammonium, phosphonium, sulfonium or sulfoxonium salts, for example ammonium salts, alkylammonium salts, such as isopropylammonium salts, tetraalkylammonium salts, benzyltriarylammonium salts, trialkylsulfonium salts or trialkylsulfoxonium salts, being preferred.

The 1,8-naphthalenedicarboximides Ia, Ib and Ic are obtainable, for example, by the following methods:

a) The compounds Ib and Ic are known and can be prepared by known processes [e.g. Prog. Clin. Biol. Res, (Enzym. Mol. Biol. Carbonyl Metab.), 232 (1987) 353; J. Med. Chem., 29 (1986), 2384; Egypt. J. Chem. 24 (1981), 127; Ind. J. Chem. Sect. B, 21B (1982), 1106; Egypt. J. Chem. 25 (1982), 445, and the literature cited there].

In general, a 1,8-naphthalenedicarboxylic anhydride of the formula VIa or a 1,4,5,8-naphthalenetetracarboxylic dianhydride of the formula VIb is condensed with an amino compound VII:

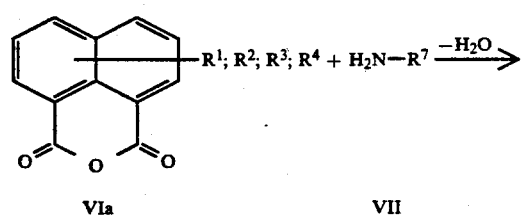

Usually, the starting materials VI and VII are used in a stoichiometric ratio, but an excess of one component or the other may be advantageous in specific cases.

The reaction temperature is in general from 0° to 250° C., advantageously in the boiling range of the solvent.

The 1,8-naphthalenedicarboximides Ib and Ic prepared in this manner can be converted by a conventional method into further derivatives Ib and Ic, respectively, so that the substitution pattern may be varied in a wide range.

b) The novel compounds Ia can advantageously be obtained by reacting an acyl halide of the formula II with an oxime III in the presence of a base:

Suitable solvents are inert aliphatic or aromatic hydrocarbons or chlorohydrocarbons, such as pyridine, toluene, chlorobenzene and methylene chloride, and ethers, such as diethyl ether, methyl tert-butyl ether, tetrahydrofuran and dioxane, or suitable mixtures of the stated solvents.

Advantageously used bases are compounds such as pyridine, 4-dimethylaminopyridine, diazabicycloundecene (DBU), diazabicyclooctane (DABCO), tertiary aliphatic amines, such as triethylamine, or (in the case of the Schotten-Baumann preparation method) aqueous alkali or alkali metal carbonate solutions.

Usually, the starting materials II and III are used in a stoichiometric ratio, but an excess of one component or the other may be advantageous in specific cases.

The reaction can be carried out at atmospheric, superatmospheric or reduced pressure by a conventional method. The reaction temperature is in general from $-10°$ to $150°$ C., in particular from $10°$ to $100°$ C. Advantageously, the reaction is effected at atmospheric pressure in the boiling range of the solvent.

When pyridine is used as the base and solvent, working up is carried out in general by pouring the reaction mixture into water or, in the case of water immiscible solvents, in general by extraction with water, washing with dilute mineral acids and neutralization. The products are purified, for example, by crystallization, reprecipitation or chromatography.

The oximes III are known or are obtainable by known processes.

Where $R^5$ and $R^6$ differ, the oximes III are generally in the form of a mixture of the syn and anti isomers, so that the end product Ia may also be obtained as an isomer mixture.

Suitable acyl halides II are the fluorides, chlorides or bromides. The acyl chlorides are particularly preferred. They are advantageously obtained by halogenating the corresponding carboxylic acids with a halogenating agent such as thionyl chloride or phosphorus trichloride or phosphorus pentachloride. The carboxylic acids are known or can be synthesized similarly to the compounds Ib.

For the preparation of the compounds Ia, other activated carboxylic acid derivatives, such as carboxylic anhydrides and carboximidazolides, may also be reacted, apart from the acyl halides II.

In view of the intended use of the compounds Ia, Ib and Ic as crop protection agents, suitable substituents are the following radicals:

$R^1$ to $R^4$ are each hydrogen, hydroxyl, mercapto, cyano, thiocyanato or nitro;

halogen, in particular fluorine, chlorine or bromine; straight-chain or branched $C_1-C_6$-alkyl or $C_1-C_6$-haloalkyl, in particular $C_1-C_4$-alkyl or $C_1-C_4$-haloalkyl, such as methyl, ethyl or tert-butyl or trifluoromethyl, pentafluoroethyl or 2-chloro-1,1,2-trifluoroethyl;

$C_2-C_6$-alkenyl, in particular $C_2-C_4$-alkenyl, such as ethenyl, 2-propenyl or 3-butenyl;

$C_2-C_6$-alkynyl, in particular $C_2-C_4$-alkynyl, eg. 2-propynyl;

$C_3-C_6$-cycloalkyl or cycloalkoxy, in particular cyclopropyl, cyclopentyl, cyclohexyl or cyclohexyloxy;

amino, $C_1-C_8$-alkylamino or di-$C_1-C_6$-alkylamino, in particular amino, $C_1-C_4$-alkylamino or di-$C_1-C_4$-alkylamino, eg. methylamino, tert-butylamino, dimethylamino, methylethylamino or diethylamino;

amino-$C_1-C_4$-alkyl, $C_1-C_6$-alkylamino-$C_1-C_4$-alkyl or di-$C_1-C_6$-alkylamino-$C_1-C_4$-alkyl, in particular amino-$C_1$- or -$C_2$-alkyl, $C_1-C_4$-alkylamino-$C_1$- or -$C_2$-alkyl or di-$C_1-C_4$-alkylamino-$C_1$-or -$C_2$-alkyl, eg. aminomethyl, methylaminomethyl, dimethylaminomethyl or methylethylaminomethyl;

$C_1-C_4$-alkoxy or $C_1-C_4$-alkylthio, eg. methoxy, ethoxy, tertbutoxy, methylthio or ethylthio;

$C_1-C_4$-alkoxy-$C_1-C_4$-alkyl or $C_1-C_4$-alkylthio-$C_1-C_4$-alkyl, in particular $C_1-C_3$-alkoxy-$C_1$- or -$C_2$-alkyl or $C_1-C_3$-alkylthio-$C_1$-or -$C_2$-alkyl, eg. methoxymethyl, methoxyethyl, ethoxymethyl, tert-butoxymethyl, methylthiomethyl or ethylthiomethyl;

$C_1-C_6$-alkylcarbonyl or $C_1-C_6$-alkylcarbonyloxy, in particular $C_1-C_4$-alkylcarbonyl or $C_1-C_4$-alkylcarbonyloxy, such as methylcarbonyl, n-butylcarbonyl, methylcarbonyloxy or tert-butylcarbonyloxy;

$C_1-C_6$-alkoxycarbonyl, in particular $C_1-C_4$-alkoxycarbonyl, such as methoxycarbonyl, ethoxycarbonyl or tert-butoxycarbonyl;

hydroxycarbonyl or hydroxycarbonyl-$C_1-C_3$-alkyl, in particular hydroxycarbonyl, hydroxycarbonylmethyl or hydroxycarbonylethyl;

hydroxycarbonyl-$C_1-C_4$-alkoxy or hydroxycarbonyl-$C_1-C_4$-alkylthio, in particular hydroxycarbonylmethoxy, hydroxycarbonylethoxy, hydroxycarbonylmethylthio or hydroxycarbonylethylthio;

hydroxysulfonyl;

$C_1-C_6$-alkylsulfinyl or $C_1-C_6$-alkylsulfonyl, in particular $C_1-C_4$-alkylsulfinyl or $C_1-C_4$-alkylsulfonyl, such as methylsulfinyl, tert-butylsulfinyl, methylsulfonyl or tertbutylsulfonyl;

$C_1-C_4$-alkoxysulfonyl, in particular methoxysulfonyl, ethoxysulfonyl or tert-butoxysulfonyl;

aminosulfonyl, $C_1-C_4$-alkylaminosulfonyl or di-$C_1-C_4$-alkylaminosulfonyl, in particular methylaminosulfonyl, ethylaminosulfonyl, tert-butylaminosulfonyl, methylethylaminosulfonyl, dimethylaminosulfonyl or diethylaminosulfonyl;

hydrazino which may carry not more than 3 $C_1-C_4$-akyl radicals, especially hydrazino;

phenyl or phenyl-$C_1-C_3$-alkyl, where the aryl moieties may carry not more than 3 of the following substituents: halogen, cyano, nitro, $C_1-C_4$-alkyl, such as methyl or ethyl, $C_1-C_4$-alkoxy, such as methoxy, amino, $C_1-C_4$-alkylamino, such as methylamino, di-$C_1-C_6$-alkylamino, such as dimethylamino, or partially or completely halogenated $C_1-C_4$-alkyl, such as trichloromethyl or trifluoromethyl, in particular phenyl, benzyl, phenylethyl or phenyl-n-propyl;

naphthyl or naphthyl-$C_1-C_3$-alkyl, where the aryl moieties may carry not more than 3 of the substituents stated for the phenyl group, in particular naphthyl, naphth-1-ylmethyl or naphth-1-ylethyl;

a 5-membered or 6-membered hetaryl or hetaryl-$C_1-C_3$-alkyl group whose hetaryl moieties may carry not more than 3 of the substituents stated above for the phenyl group, in particular 2-pyrrolyl, 2-thienyl, 3-furanyl or 2-pyridyl; phenoxy or naphthyloxy which may carry not more than 3 of the substituents stated above for the phenyl group, in particular phenoxy or naphthyloxy;

phenylthio or naphthylthio, each of which may carry not more than 3 of the substituents stated above for the phenyl group, in particular phenylthio or naphthylthio;

phenoxycarbonyl or naphthyloxycarbonyl, each of which may carry not more than 3 of the substituents stated above for the phenyl group, in particular phenoxycarbonyl or naphthyloxycarbonyl;

phenylcarbonyl or naphthylcarbonyl, each of which may carry not more than 3 of the substituents stated above for the phenyl group, in particular phenylcarbonyl or naphthylcarbonyl;

phenylcarbonyloxy or napthylcarbonyloxy, each of which may carry not more than 3 of the substituents stated above for the phenyl group, in particular phenylcarbonyloxy or naphthylcarbonyloxy;

phenyl-$C_1$-$C_3$-alkoxy or naphthyl-$C_1$-$C_3$-alkoxy, which may carry not more than 3 of the substituents stated above for the phenyl group, in particular phenyl-$C_1$ or -$C_2$-alkoxy or naphthyl-$C_1$-$C_3$-alkoxy, eg. phenylmethoxy or naphth-1-ylmethoxy;

a 5-membered or 6-membered hetaryl-$C_1$-$C_3$-alkoxy group which may carry not more than 3 of the substituents stated above for the phenyl group, in particular pyrrolylmethoxy;

phenylsulfinyl or naphthylsulfinyl, each of which may carry not more than 3 of the substituents stated above for the phenyl group, in particular phenylsulfinyl or naphthylsulfinyl;

a 5-membered or 6-membered hetarylsulfinyl or hetarylsulfonyl group which may carry not more than 3 of the substituents stated above for the phenyl group;

phenylsulfonyl or naphthylsulfonyl, each of which may carry not more than 3 of the substituents stated above for the phenyl group, in particular phenylsulfonyl or naphthylsulfonyl;

phenoxysulfonyl or naphthyloxysulfonyl, each of which may carry not more than 3 of the substituents stated above for the phenyl group, in particular phenoxysulfonyl or naphthyloxysulfonyl, or a 5-membered or 6-membered hetaryloxysulfonyl group which may carry not more than 3 of the substituents stated above for the phenyl group;

X is a $C_1$-$C_6$-alkylene chain which may furthermore carry one of the following radicals: halogen, such as fluorine, chlorine or bromine, hydroxyl, mercapto, $C_1$-$C_4$-alkyl, such as methyl or tert-butyl, $C_1$-$C_4$-alkoxy, $C_1$-$C_4$-alkylthio, di-$C_1$-$C_4$-alkylamino, $C_1$-$C_4$-alkoxycarbonyl, cyano, $C_1$-$C_6$-alkylcarbonyl, $C_1$-$C_6$-alkylcarbonyloxy, phenyl, naphthyl, 5-membered or 6-membered hetaryl, phenyl-$C_1$-$C_3$-alkyl, naphthyl-$C_1$-$C_3$-alkyl or 5-membered or 6-membered hetaryl-$C_1$-$C_3$-alkyl, where the aryl and hetaryl moieties of the 6 last-mentioned radicals may furthermore carry not more than 3 halogen atoms or $C_1$-$C_4$-alkyl groups;

$R^5$ is hydrogen or cyano;

straight-chain or branched $C_1$-$C_6$-alkyl, in particular $C_1$-$C_4$-alkyl, such as methyl, ethyl, n-propyl, isopropyl, n-butyl or tert-butyl;

$C_2$-$C_6$-alkenyl, in particular $C_2$-$C_4$-alkenyl, such as ethenyl or 3-butenyl;

$C_1$-$C_4$-alkoxy-$C_1$-$C_4$-alkyl or $C_1$-$C_4$-alkylthio-$C_1$-$C_4$-alkyl, in particular $C_1$-$C_3$-alkoxy-$C_1$- or -$C_2$-alkyl or $C_1$-$C_3$-alkylthio-$C_1$-or -$C_2$-alkyl, eg. methoxymethyl, ethoxyethyl or methylthiomethyl;

$C_1$-$C_4$-alkoxycarbonyl, in particular methoxycarbonyl or ethoxycarbonyl;

acetyl;

$C_3$-$C_6$-cycloalkyl, in particular cyclopropyl, cyclopentyl or cyclohexyl;

benzoyl, naphthoyl or a 5-membered or 6-membered hetaroyl group, in particular benzoyl, naphthoyl, pyridylcarbonyl or thienylcarbonyl;

phenyl or naphthyl, each of which may carry not more than 3 of the following radicals: halogen, such as fluorine, chlorine or bromine, hydroxyl, cyano, trifluoromethyl, straight-chain or branched $C_1$-$C_6$-alkyl, $C_1$-$C_6$-alkoxy, partially or completely substituted $C_1$-$C_6$-alkoxy, $C_1$-$C_6$-alkylthio, di-$C_1$-$C_3$-alkylamino or acetylamino, in particular phenyl or naphthyl;

phenyl-$C_1$-$C_3$-alkyl or naphthyl-$C_1$-$C_3$-alkyl, which may carry not more than 3 of the radicals stated for the phenyl group, in particular benzyl, phenethyl or naphth-1-ylmethyl, or a 5-membered or 6-membered hetaryl or hetaryl-$C_1$-$C_3$-alkyl group which may carry not more than 3 of the radicals stated above for the phenyl group, in particular 2-pyrrolyl, 2-thienyl, 3-furanyl or 2-pyridyl;

$R^6$ is hydrogen or cyano;

straight-chain or branched $C_1$-$C_6$-alkyl or $C_1$-$C_6$-haloalkyl, in particular $C_1$-$C_4$-alkyl or $C_1$-$C_4$-haloalkyl, eg. methyl, ethyl, n-propyl, isopropyl, n-butyl, tert-butyl, trifluoromethyl, pentafluoroethyl or 2-chloro-1,1,2-trifluoroethyl;

$C_1$-$C_4$-alkoxy, in particular methoxy, ethoxy or tert-butoxy;

$C_1$-$C_4$-alkoxy-$C_1$-$C_4$-alkyl, in particular $C_1$-$C_3$-alkoxy-$C_1$- or -$C_2$-alkyl, eg. methoxymethyl, ethoxymethyl or methoxyethyl;

diazolylmethyl- or triazolylmethyl, in particular 1,3-diazol-1-ylmethyl, 1,2-diazol-1-ylmethyl, 1,2,4-triazol-1-ylmethyl or 1,3,4-triazol-1-yl-methyl;

$C_1$-$C_6$-alkoxycarbonyl, in particular $C_1$-$C_4$-alkoxycarbonyl, eg. methoxycarbonyl, ethoxycarbonyl or tert-butoxycarbonyl;

furyl or tetrahydrofuryl;

tetrahydropyranyl or tetrahydrothiopyranyl;

thienyl;

dihydropyranyl or dihydrothiopyranyl, or phenyl, if $R^5$ is hydrogen, methyl or acetyl, with the proviso that $R^5$ and $R^6$ are not simultaneously hydrogen, or, together with $R^5$ and the common carbon atom, $C_3$-$C_{12}$-cycloalkyl, in particular cyclopropyl, cyclopentyl, cyclohexyl, cycloheptyl and cyclododecyl;

a 5-membered or 6-membered ring which may be saturated or partially or completely unsaturated and may contain an oxygen or sulfur atom as a hetero atom and which may furthermore carry not more than 3 $C_1$-$C_3$-alkyl or $C_1$-$C_3$-alkoxy groups or a fused-on benzene ring, in particular 3,3,5-trimethylcyclohexylidene, 3-methylcyclopentylidene, 3-methylcyclohexylidene, 3-methylcyclopent-2-enylidene, cyclohex-2-enylidene,2-methoxycyclohex-2-enylidene,2,6-dimethylpyran-4-ylidene, 2,6-dimethylthiopyran-4-ylidene, tetrahydropyran-4-ylidene, tetrahydrothiopyran-4-ylidene, 2,3-benzocyclopent-1-vlid-ene or 2,3-benzocyclohex-2-ylidene, and $R^7$ is hydrogen, hydroxyl or cyano;

straight-chain or branched $C_1$-$C_6$-alkyl or $C_1$-$C_6$-haloalkyl, in particular $C_1$-$C_4$-alkyl or $C_1$-$C_4$-haloalkyl, such as methyl, ethyl, n-propyl, tert-butyl, trifluoromethyl, pentafluoroethyl or 2-chloro-1,1,2-trifluoroethyl;

$C_1$-$C_6$-hydroxyalkyl, in particular $C_1$-$C_4$-hydroxyalkyl, such as hydroxymethyl, hydroxyethyl, 4-hydroxy-n-but-1-yl or 2-hydroxy-1,1-dimethylethyl;

$C_2$-$C_6$-alkenyl, in particular $C_2$-$C_4$-alkenyl, such as ethenyl, 2-propen-1-yl or but-3-enyl;

$C_1$-$C_4$-alkoxy, in particular methoxy, ethoxy, isopropoxy or n-butoxy;

$C_1$-$C_4$-alkoxy-$C_1$-$C_4$-alkyl, in particular $C_1$-$C_3$- alkoxy-$C_1$ or -$C_2$-alkyl, eg. methoxymethyl, methoxyethyl, ethoxymethyl $C_1$-$C_4$-alkylthio-$C_1$-$C_4$-alkyl, in particular $C_1$-$C_3$-alkylthio-$C_1$ or -$C_2$-alkyl, such as methylthiomethyl, methylthioethyl or ethylthiomethyl;

amino, $C_1$–$C_4$-alkylamino or di-$C_1$–$C_4$-alkylamino, in particular amino, methylamino, tert-butylamino, dimethylamino, diethylamino or methylethylamino;

$C_3$–$C_8$-cycloalkyl or $C_3$–$C_8$-cycloalkoxy, in particular cyclopropyl, cyclopentyl, cyclohexyl, cyclopentyloxy or cyclohexyloxy;

acyl;

$C_1$–$C_4$-alkoxycarbonyl-$C_1$–$C_6$-alkyl, in particular $C_1$–$C_3$-alkoxycarbonyl-$C_1$–$C_2$-alkyl, eg. methoxycarbonylmethyl, ethoxycarbonylmethyl, n-propoxycarbonylmethyl or ethoxycarbonylethyl;

aminocarbonyl-$C_1$–$C_6$-alkyl, $C_1$–$C_4$-alkylaminocarbonyl-$C_1$–$C_6$-alkyl or di-$C_1$–$C_4$-alkylaminocarbonyl-$C_1$–$C_6$-alkyl, in particular aminocarbonyl-$C_1$- or -$C_2$-alkyl, $C_1$–$C_3$-alkylaminocarbonyl-$C_1$- or -$C_2$-alkyl or di-$C_1$–$C_3$-alkylaminocarbonyl-$C_1$- or -$C_2$-alkyl, eg. aminocarbonylmethyl, methylaminocarbonylmethyl, dimethylaminocarbonylmethyl, aminocarbonylethyl or diethylaminocarbonylethyl;

$C_1$–$C_4$-alkoxyaminocarbonyl-$C_1$–$C_6$-alkyl or N-$C_1$–$C_4$-alkoxy-N-$C_1$–$C_4$-alkylaminocarbonyl-$C_1$–$C_6$-alkyl, in particular $C_1$–$C_3$-alkoxyaminocarbonyl-$C_1$- or -$C_2$-alkyl or N-$C_1$–$C_3$-alkoxy-N-$C_1$–$C_3$-alkylaminocarbonyl-$C_1$- or -$C_2$-alkyl, eg. methoxyaminocarbonylmethyl, N-methoxy-N-methylaminocarbonylmethyl or N-ethoxy-N-ethylaminocarbonylethyl;

$C_1$–$C_4$-alkylthiocarbonyl-$C_1$–$C_6$-alkyl, in particular $C_1$–$C_3$-alkylthiocarbonyl-$C_1$- or -$C_2$-alkyl, eg. methylthiocarbonylmethyl or ethylthiocarbonylethyl;

$C_1$–$C_4$-alkoxycarbonyl or $C_1$–$C_4$-alkylcarbonyloxy, in particular methoxycarbonyl;

$C_1$–$C_4$-alkoxysulfonyl-$C_1$–$C_6$-alkyl, in particular $C_1$–$C_3$-alkoxysulfonyl-$C_1$- or -$C_2$-alkyl, eg. methoxysulfonylmethyl, methoxysulfonylethyl or n-propoxysulfonylethyl; aminosulfonyl-$C_1$–$C_6$-alkyl, $C_1$–$C_4$-alkylaminosulfonyl-$C_1$–$C_6$-alkyl or di-$C_1$–$C_4$-alkylaminosulfonyl-$C_1$–$C_6$-alkyl, in particular aminosulfonyl-$C_1$- or -$C_2$-alkyl, $C_1$–$C_3$-alkylaminosulfonyl-$C_1$- or -$C_2$-alkyl or di-$C_1$–$C_3$-alkylaminosulfonyl-$C_1$- or -$C_2$-alkyl, eg. aminosulfonylmethyl, dimethylaminosulfonylmethyl ordiethylaminosulfonylethyl;

hydroxycarbonyl-$C_1$–$C_6$-alkyl or hydroxycarbonyl-$C_1$–$C_6$-alkoxy, in particular hydroxycarbonyl-$C_1$- or -$C_2$-alkyl or hydroxycaroonyl-$C_1$- or -$C_2$-alkoxy, such as hydroxycarbonylmethyl, hydroxycarbonylethyl or hydroxycarbonylmethoxy;

hydroxysulfonyl-$C_1$–$C_6$-alkyl, in particular hydroxysulfonyl-$C_1$–$C_2$-alkyl, such as hydroxysulfonylmethyl or hydroxysulfonylethyl;

phenyl or phenyl-$C_1$–$C_4$-alkyl, where the aromatic moiety in each case may carr-y not more than 3 halogen atoms or $C_1$–$C_4$-alkyl groups or one of the following radicals: nitro, cyano, hydroxycarbonyl, amino, $C_1$–$C_4$-alkylamino, di-$C_1$–$C_4$-alkylamino, $C_1$–$C_4$-alkoxy or partially or completely halogenated $C_1$–$C_4$-alkyl, in particular phenyl, benzyl, phenethyl or 4-phenylbutyl;

naphthyl or naphthyl-$C_1$–$C_4$-alkyl, where the aromatic moiety in each case may carry not more than 3 halogen atoms or $C_1$–$C_4$-alkyl groups or one of the radicals stated for the above phenyl group, in particular naphthyl, naphth-1-ylmethyl or naphth-1-yleth-2-yl;

a 5-membered or 6-membered hetaryl or hetaryl-$C_1$–$C_4$-alkyl group, where the aromatic moiety in each case may carry not more than 3 halogen atoms or $C_1$–$C_4$-alkyl groups or one of the radicals stated for the above phenyl group, in particular pyrrolyl, thienyl, furanyl, pyridyl, 2-pyridylmethyl, 3-pyridylmethyl or 4-pyridylmethyl;

phenoxy or phenyl-$C_1$–$C_4$-alkoxy, where the aromatic moiety in each case may carry not more than 3 halogen atoms or $C_1$–$C_4$-alkyl groups or one of the radicals stated for the above phenyl group in particular phenoxy, benzyloxy, 2-phenylethoxy or 4-phenylbutoxy;

naphthyloxy or naphthyl-$C_1$–$C_4$-alkoxy, where the aromatic moiety in each case may carry not more than 3 halogen atoms or $C_1$–$C_4$-alkyl groups or one of the radicals stated for the above phenyl group, in particular naphthyloxy, naphth-1-ylmethoxy or 4-(naphth-1-yl)-butoxy;

benzoyl which may furthermore carry not more than 3 halogen atoms or $C_1$–$C_4$-alkyl groups or one of the radicals stated for the above phenyl group;

phenoxycarbonyl-$C_1$–$C_4$-alkyl or naphthyloxycarbonyl-$C_1$–$C_4$-alkyl, where the aromatic moiety in each case may furthermore carry not more than 3 halogen atoms or $C_1$–$C_4$-alkyl groups or one of the radicals stated for the above phenyl group, in particular phenoxycarbonylmethyl, 4-(phenoxycarbonyl)-butyl, 1-naphthyloxycarbonylmethyl or 4-(1-naphthyloxycarbonyl)-butyl;

a 5-membered or 6-membered hetaryloxycarbonyl-$C_1$–$C_4$-alkyl group, where the aromatic moiety in each case may furthermore carry not more than 3 halogen atoms or $C_1$–$C_4$-alkyl groups or one of the radicals stated for the above phenyl group, in particular 3-pyridyloxycarbonyl or thienyloxycarbonyl;

—$(CH_2)_n$—COO—$NR^8R^9$, where n is an integer of from 1 to 6 and $R^8$ and $R^9$ are each $C_1$–$C_3$-alkyl, in particular methyl or ethyl, or $C_1$–$C_3$-alkylcarbonyl, in particular methylcarbonyl, especially —$(CH_2)_2$—COO—$N(CH_3)(CO—CH_3)$, or —$(CH_2)_n$—COO—$NR^8R^9$, where n is an integer from 1 to 6 and $R^8$ and $R^9$, together with the common nitrogen atom, form a 5-membered or 6-membered ring, in particular pyrrolidin-1-yloxycarbonyl or 2-(pyrrolidin-1-yloxycarbonyl)-ethyl.

Particularly suitable compounds Ia, Ib and Ic are shown in Tables 1, 2 and 3.

Specific examples of herbicidal hetaryloxy- or aryloxyphenoxyacetic acid derivatives of the formula IV whose toleration by crops can be improved by substituted 1,8-naphthalenedicarboximides of the formulae Ia, Ib and/or Ic are shown in Table A below:

TABLE A $$R^a-O-\underset{}{\underset{}{\bigcirc}}-O-\underset{R^c}{\underset{|}{CH}}-CO_2R^b \quad IV$$

| No. | $R^a$ | $R^b$ | $R^c$ | Reference |
|---|---|---|---|---|
| IV.1 | (2,4-dichlorophenyl) | $CH_3$ | $CH_3$ | DE-A 22 23 894 |
| IV.2 | (5-trifluoromethyl-2-pyridyl) | n-$C_4H_9$ | $CH_3$ | BE-A 868 875 |

TABLE A-continued $$R^a-O-\text{\textlangle}C_6H_4\text{\textrangle}-O-\overset{R^c}{\underset{}{C}}H-CO_2R^b \quad \text{IV}$$

| No. | $R^a$ | $R^b$ | $R^c$ | Reference |
|---|---|---|---|---|
| IV.3 | 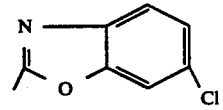 | $C_2H_5$ | $CH_3$ | BE-A 858 618 |
| IV.4 | 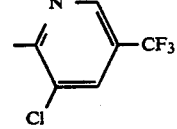 | $CH_3$ | $CH_3$ | BE-A 868 875 |
| IV.5 | 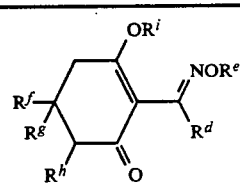 | $C_2H_5$ | $CH_3$ | DE-A 30 04 770 |

Specific examples of herbicidal cyclohexenones of the formula V whose toleration by crops can be improved by substituted 1,8-napthalenedicarboximides of the formula Ia, Ib and/or Ic are shown in Tables B and C below

TABLE B

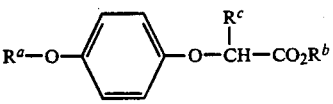

| No. | $R^d$ | $R^e$ | $R^f$ | $R^g$ | $R^h$ | $R^i$ | Reference |
|---|---|---|---|---|---|---|---|
| V.1 | $C_3H_7$ | $CH_2CH=CH_2$ | $CH_3$ | $CH_3$ | $CO_2CH_3$ | Na | DE-A 2 439 104 |
| V.2 | $C_3H_7$ | $CH_2CH_3$ | $CH_2CH(CH_3)SCH_2CH_3$ | H | H | H | DE-A 2 822 304 |
| V.3 | $C_2H_5$ | $CH_2CH=CHCl$ | $CH_2CH(CH_3)SCH_2CH_3$ | H | H | H | US-A 4 440 566 |
| V.4 | $C_3H_7$ | $CH_2CH=CHCl$ | $CH_2CH(CH_3)SCH_2CH_3$ | H | H | H | US-A 4 440 566 |
| V.5 | $C_3H_7$ | $C_2H_5$ | 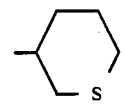 | H | H | H | EP-A 71 707 |
| V.6 | $C_2H_5$ | $C_2H_5$ | 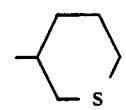 | H | H | H | EP-A 71 707 |
| V.7 | $CH_3$ | $CH_2CH=CHCH_3$ | 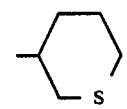 | H | H | H | EP-A 71 707 |
| V.8 | $C_3H_7$ | $C_2H_5$ | 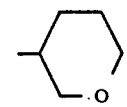 | H | H | H | EP-A 71 707 |
| V.9 | $C_2H_5$ | $CH_2CH=CHCl$ | 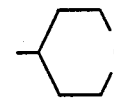 | H | H | H | EP-A 142 741 |
| V.10 | $C_3H_7$ | $C_2H_5$ | 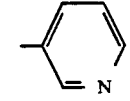 | H | H | H | EP-A 66 195 |

TABLE B-continued

V structure: cyclohexenone with OR^i, =NOR^e, R^d, R^f, R^g, R^h substituents

| No. | R^d | R^e | R^f | R^g | R^h | R^i | Reference |
|---|---|---|---|---|---|---|---|
| V.11 | C₂H₅ | C₂H₅ | 4-CH₃-phenyl | H | H | H | DE-A 24 39 104 |
| V.12 | C₂H₅ | CH₂CH=CHCH₃ | 4-C₂H₅-phenyl | H | H | H | DE-A 38 08 072 |
| V.13 | C₂H₅ | C₂H₅ | 2,4,5-tri-CH₃-phenyl | H | H | H | EP-A 880 301 |
| V.14 | C₃H₇ | CH₂CH=CHCl | 4-CH₃-cyclohexyl | H | H | H | EP-A 88 299 |
| V.15 | C₃H₇ | CH₂CH=CHCH₃ | 4-CH₃-cyclohexyl | H | H | H | EP-A 88 299 |
| V.16 | C₂H₅ | CH₂CH=CHCH₃ | 3-CH(CH₃)₂-5-methyl-isoxazolyl | H | H | H | EP-A 238 021 |
| V.17 | C₃H₇ | CH₂CH=CHCH₃ | 3-CH(CH₃)₂-5-methyl-isoxazolyl | H | H | H | EP-A 238 021 |
| V.18 | C₂H₅ | CH₂CH=CHCl | 4-(OCH₂—C≡CH)-phenyl | H | H | H | EP-A 137 174 |
| V.19 | C₃H₇ | C₂H₅ | 4-(CH₂OC₂H₅)-phenyl | H | H | H | EP-A 2 137 200 |
| V.20 | C₃H₇ | C₂H₅ | 3,4-dibromo-tetrahydropyranyl | H | H | H | EP-A 230 235 |
| V.21 | C₃H₇ | CH₂CH=CHCl | 3,4-dibromo-tetrahydropyranyl | H | H | H | EP-A 230 235 |

TABLE B-continued $$\underset{\underset{R^h}{\overset{R^g}{\big|}}}{\underset{R^f}{\big|}} \text{cyclohexenone with } OR^i, =NOR^e, R^d \text{ substituents}$$ V

| No. | $R^d$ | $R^e$ | $R^f$ | $R^g$ | $R^h$ | $R^i$ | Reference |
|---|---|---|---|---|---|---|---|
| V.22 | $C_3H_7$ | $CH_2CH=CHCl$ | 2,6,6-trimethylcyclohex-1-enyl | H | H | H | EP-A 46 860 |
| V.23 | $C_3H_7$ | $C_2H_5$ | cyclohexyl | H | H | H | JP-A 540 191 945 |
| V.24 | $C_3H_7$ | $C_2H_5$ | cyclohex-1-enyl | H | H | H | EP-A 46 860 |
| V.25 | $CH_3$ | $CH_2CH=CHCl$ | 4-methylcyclohexyl | H | H | H | EP-A 88 299 |
| V.26 | $C_3H_7$ | $C_2H_5$ | 4-(trifluoromethyl)phenyl | H | H | K | EP-A 137 174 |
| V.27 | $C_2H_5$ | $CH_2CH=CHCl$ | 2,6,6-trimethylcyclohex-1-enyl | H | H | H | EP-A 46 860 |
| V.28 | $C_3H_7$ | $CH_2CH=CHCH_3$ | 2,4-dimethylthiazol-5-yl | H | H | H | EP-A 125 094 |
| V.29 | $C_3H_7$ | $CH_2CH=CHCl$ | 2,4-dimethylthiazol-5-yl | H | H | H | EP-A 125 094 |
| V.30 | $C_3H_7$ | $C_2H_5$ | 2,4,6-trimethylcyclohexyl | H | H | H | EP-A 88 299 |

TABLE B-continued $$\underset{\substack{R^f\\R^g\\R^h}}{\overset{OR^i}{\diagdown}}\text{cyclohexenone with }=NOR^e, R^d\text{ substituent}$$

V

| No. | $R^d$ | $R^e$ | $R^f$ | $R^g$ | $R^h$ | $R^i$ | Reference |
|---|---|---|---|---|---|---|---|
| V.31 | $C_3H_7$ | $CH_2CH=CH_2$ | cyclohexyl with HO, $H_3C$, $H_5C_2S$ | H | H | H | EP-A 228 598 |
| V.32 | $C_2H_5$ | $C_2H_5$ | cyclohexyl with HO, HO | H | H | H | EP-A 228 598 |
| V.33 | $C_3H_7$ | $C_2H_5$ | N-methylpyrazolyl | H | H | H | EP-A 66 195 |
| V.34 | $C_3H_7$ | $CH_2CH=CHCl$ | N-methylpyrrolyl | H | H | H | EP-A 66195 |
| V.35 | $C_3H_7$ | $CH_2CH=CH_2$ | methylthiazoline | H | H | H | EP-A 125 094 |
| V.36 | $C_3H_7$ | $C_3H_7$ | $CH(SCH_2CH_3)_2$ | H | H | H | EP-A 230 260 |
| V.37 | $C_3H_7$ | $C_2H_5$ | thianyl S-oxide | H | H | H | EP-A 115 808 |
| V.38 | $C_3H_7$ | $C_2H_5$ | thianyl S,S-dioxide | H | H | H | EP-A 115 808 |
| V.39 | $C_3H_7$ | $C_2H_5$ | $CH_3$ | $CH_3$ | $C(CH_3)=NOCH_3$ | H | EP-A 172 551 |
| V.40 | $C_3H_7$ | $CH_2CH=CH_2$ | thianyl S,S-dioxide | OH | H | H | Proceedings Brit. Crop-Protection Conference weeds 1985 Vol. 1 Pages 93–98 |
| V.41 | $C_2H_5$ | $CH_2CH=CH-CH_2-C_6H_4-Cl$ | thianyl | H | H | H | EP-A 89 120 558.2 |

TABLE B-continued

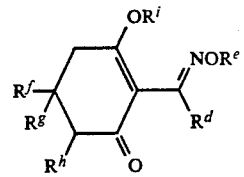

| No. | $R^d$ | $R^e$ | $R^f$ | $R^g$ | $R^h$ | $R^i$ | Reference |
|---|---|---|---|---|---|---|---|
| V.42 | $C_2H_5$ | $CH_2CH_2-CH=CH-$(4-Cl-C$_6$H$_4$) | 3-tetrahydrothiopyranyl | H | H | H | EP-A 89 120 558.2 |
| V.43 | $C_2H_5$ | $CH_2CH_2-CH=CH-$(4-F-C$_6$H$_4$) | 3-tetrahydrothiopyranyl | H | H | H | EP-A 89 120 558.2 |
| V.44 | n-$C_3H_7$ | $CH_2CH_2-CH=CH-$(4-F-C$_6$H$_4$) | 3-tetrahydrothiopyranyl | H | H | H | EP-A 89 120 558.2 |
| V.45 | n-$C_2H_5$ | $CH_2CH=CH-CH_2-$C$_6$H$_5$ | 3-tetrahydrothiopyranyl | H | H | H | |
| V.46 | n-$C_3H_7$ | $CH_2$-(5-Cl-2-thienyl) | 3-tetrahydrothiopyranyl | H | H | H | EP-A 177 913 |
| V.47 | $C_2H_5$ | $CH_2$-(5-Cl-2-thienyl) | 3-tetrahydrothiopyranyl | H | H | H | EP-A 177 193 |
| V.48 | $C_2H_5$ | $CH_2$-(5-Cl-2-thienyl) | 3-tetrahydropyranyl | H | H | H | EP-A 177 913 |
| V.49 | n-$C_3H_7$ | $CH_2$-(5-Cl-2-thienyl) | 4-tetrahydropyranyl | H | H | H | EP-A 177 913 |
| V.50 | n-$C_3H_7$ | $CH_2$-(5-Cl-2-thienyl) | 4-tetrahydrothiopyranyl | H | H | H | EP-A 177 913 |
| V.51 | $CH_3$ | $CH_2$-(5-Cl-2-thienyl) | 4-tetrahydropyranyl | H | H | H | EP-A 177 913 |
| V.52 | $C_2H_5$ | $CH_2$-(5-Cl-2-thienyl) | 4-tetrahydropyranyl | H | H | H | EP-A 177 913 |

TABLE C

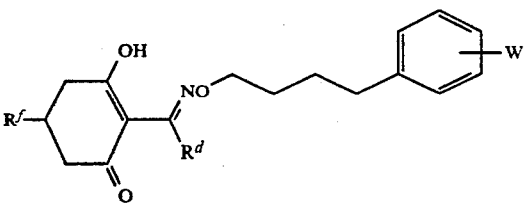

V

| No. | $R^d$ | $R^f$ | W | Phys. data ($^1$H-NMR* [δ in ppm]) |
|---|---|---|---|---|
| V.53 | ethyl | tetrahydropyran-3-yl | 4-fluoro | 2.9 (broad, 2H); 4.1 (broad, 2H) |
| V.54 | n-propyl | tetrahydropyran-3-yl | 4-fluoro | 2.9 (t, 2H); 4.05 (broad, 2H) |
| V.55 | ethyl | tetrahydrothiopyran-3-yl | 4-fluoro | 2.9 (t, 2H); 4.05 (broad, 2H) |
| V.56 | n-propyl | tetrahydrothiopyran-3-yl | 4-fluoro | 2.9 (t, 2H); 4.05 (broad, 2H) |
| V.57 | ethyl | tetrahydropyran-4-yl | 4-fluoro | 4.05 (broad, 2H) |
| V.58 | n-propyl | tetrahydropyran-4-yl | 4-fluoro | 4.05 (broad, 2H) |
| V.59 | ethyl | tetrahydropyran-3-yl | 4-Cl | 2.9 (t, 2H); 4.05 (broad, 2H) |
| V.60 | n-propyl | tetrahydropyran-3-yl | 4-Cl | 2.9 (t, 2H); 4.05 (broad, 2H) |
| V.61 | ethyl | tetrahydropyran-4-yl | 4-Cl | 2.9 (t, 2H); 4.05 (broad, 2H) |
| V.62 | n-propyl | tetrahydropyran-4-yl | 4-Cl | 2.9 (broad, 2H); 4.05 (broad, 2H) |
| V.63 | ethyl | tetrahydrothiopyran-3-yl | 4-Cl | 4.05 (broad, 2H) |
| V.64 | n-propyl | tetrahydrothiopyran-3-yl | 4-Cl | 4.05 (broad, 2H) |

*selected signals

Herbicidal active ingredients and antidote compounds can be applied together or separately to the leaves and shoots of the crops and of the undesirable grasses, after emergence. Preferably, the antidote is applied simultaneously with the herbicidal active ingredient. Separate application, where the antidote is first applied to the field, followed by the herbicidal active ingredient, is also possible. The herbicidal active ingredient and the antidote may be a spraying agent and may be formulated together or separately in suspendable, emulsifiable or soluble form.

It is also possible for the seeds of the crops or seedlings to be treated with the antidote prior to sowing or before planting out. The herbicidal active ingredient is then applied alone or in a conventional manner.

In seed dressing, usually 0.1–10 g, preferably 1–2 g, of antidote are required per kg of seed.

In the application of the antidote by seed swelling or by treating the seedlings, solutions which contain the antidote in a concentration of from 1 to 10,000 ppm, preferably from 100 to 10,000 ppm, are particularly suitable.

For herbicidal hetaryloxy- or aryloxyphenoxyacetic acid derivatives, different amounts of an antidote compound are required if the herbicide is used in different crops. The ratios can be varied within wide ranges. They are also dependent on the structure of the hetaryloxy- or aryloxyphenoxyacetic acid derivatives and on the particular target crop. Suitable weight ratios of herbicidal active ingredient to antidote compound are from 1:10 to 1:0.01, preferably from 1:4 to 1:0.1.

For the same cyclohexenone derivative, different amounts of an antidote compound are required if the cyclohexenone derivative is used in different crops. The ratios in which the cyclohexenone derivative and a 1,8-naphthalenedicarboximide Ia and/or Ib are used can be varied within wide ranges. They are dependent on the structure of the cyclohexenone derivative and of the 1,8-naphthalenedicarboximide Ia and/or Ib and on the particular crop. Suitable weight ratios of herbicidal active ingredient to antidote compound are from 1:10 to 1:0.01, preferably from 1:4 to 1:0.25.

In addition to the substituted 1,8-naphthalenedicarboximide Ia and/or Ib and/or Ic as an antidote and the herbicide from the group consisting of the hetaryloxy- and aryloxyphenoxyacetic acids IV and of the cyclohexenones V, the novel herbicides may contain further herbicidal or growth-regulating active ingredients of different chemical structure, the antagonistic effect being retained.

The novel agents or, in the case of separate application, the herbicidal active ingredients or the antidote are applied, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend entirely on the intended uses.

For the preparation of directly sprayable solutions, emulsions, pastes and oil dispersions, mineral oil fractions having a medium to high boiling point, such as kerosene or diesel oil and coal tar oils, oils of vegetable or animal origin, aliphatic, cyclic or aromatic hydrocarbons, eg. benzene, toluene, xylene, paraffin, tetrahydronaphthalene, alkylated naphthalenes or their derivatives, eg. methanol, ethanol, propanol, butanol, chloroform, carbon tetrachloride, cyclohexanol, cyclohexanone, chlorobenzene or isophorone, and highly polar solvents, eg. dimethylformamide, dimethyl sulfoxide, N-methylpyrrolidone and water, are suitable.

Aqueous application forms can be prepared from emulsion concentrates, pastes, wettable powders or oil dispersions by the addition of water. For the preparation of emulsions, pastes or oil dispersions, the herbicidal active ingredient and/or the antidote, as such or dissolved in an oil or solvent, can be homogenized in water using wetting agents, adhesives, dispersants or emulsifiers. However, it is also possible to prepare concentrates which consist of the herbicidal active ingredient and/or the antidote and wetting agents, adhesives, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensates of sulfonated naphthalene and naphthalene derivatives with formaldehyde, condensates of naphthalene and of naphthalenesulfonic acids with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfate waste liquors and methylcellulose.

Powders, broadcasting agents and dusting agents can be prepared by mixing or milling the herbicidal active ingredient and/or the antidote together with a solid carrier.

Granules, for example coated, impregnated and homogenous granules, can be prepared by binding the active ingredients to solid carriers. Examples of solid carriers are minerals, such as silica gel, silicas, silicates, talc, kaolin, attaclay, limestone, chalk, bole, loess, clay, dolomite, kieselguhr, calcium sulfate, magnesium sulfate, magnesium oxide and milled plastics, fertilizers, eg. ammonium sulfate, ammonium phosphate, ammonium nitrate and ureas, and vegetable products, such as cereal meals, ground bark, woodmeal, nutshell meal and cellulose powder, and other solid carriers.

The formulations contain from 0.1 to 95, preferably from 0.5 to 90, % by weight of herbicidal active ingredient and antidote. The application rates of the herbicidal active ingredient are from 0.2 to 5 kg/ha.

The Examples which follow illustrate the invention.

PREPARATION EXAMPLES

Example 1

N-(2-Propyleneiminooxycarbonylmethyl)-1,8-naphthalenedicarboximide

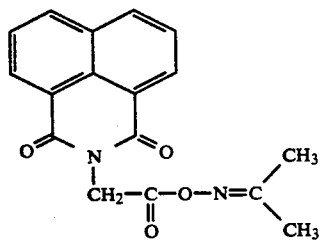

Stage 1.1: Preparation of the acyl chloride

A stirred mixture of 12.8 g (50 mmol) of N-hydroxycarbonylmethyl-1,8-naphthalenedicarboximide, 9.9 g (47.5 mmol) of phosphorus pentachloride and 20 ml of $POCl_3$ was slowly heated to 75° C. and stirred at this temperature for a further 3 hours. Thereafter, the reaction mixture was evaporated to dryness and the crude product was further processed in the following stage, without purification.

Stage 1.2: Condensation of the acyl chloride with acetone oxime

The acyl chloride obtained in stage 1.1 was introduced a little at a time, at 0° C., into a solution of 4.0 g (55 mmol) of acetone oxime and 50 ml of pyridine, after which the resulting suspension was stirred for a further 12 hours at 20° C. Thereafter, the reaction mixture was poured onto a mixture of 100 ml of ice water and 50 ml of glacial acetic acid, and the resulting precipitate was washed with 10% strength by weight sodium bicarbonate solution. Yield: 81%, mp. 107°–109° C.

Example 2

N-(Cyclohexylideneiminooxycarbonylmethyl)-1,8-naphthalenedicarboximide

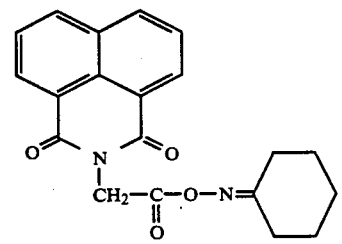

The acyl chloride obtained in stage 1.1 was reacted with 6.2 g (55 mmol) of cyclohexanone oxime similarly to Example 1.2. Yield: 71%, mp.: 184°–185° C.

Example 3

N-(1-Methyl-1-ethoxymethyleneiminoxycarbonylmethyl)-1,8-naphthalenedicarboximide

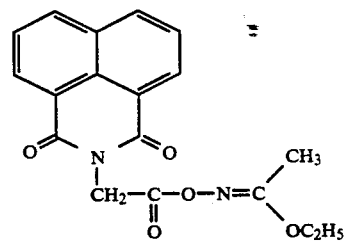

The acyl chloride obtained in stage 1.1 was reacted with 5.9 g (55 mmol) of ethoxyacethydroxamic acid similarly to Example 1.2. After hydrolysis with ice water/glacial acetic acid, the total mixture was evaporated to dryness. Thereafter, the residue was taken up in aqueous sodium bicarbonate solution and the solution was extracted with three times 120 ml of ethyl acetate. After the combined extracts had been evaporated down, the remaining solid was recrystallized from ethanol. Yield: 10% (E/Z isomer mixture), mp.: 120°–125° C.

Example 4

N-(Benzylideneiminooxycarbon-vlmethyl)-1,8-naphthalenedicarboximide

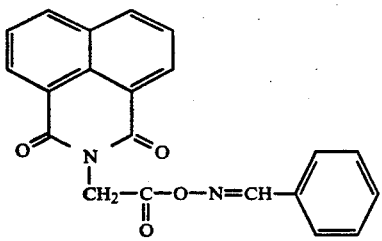

The acyl chloride obtained in stage 1.1 was added to 6.7 g (55 mmol) of benzaldoxime in 50 ml of pyridine, similarly to Example 1.2. Thereafter, the mixture was stirred for 60 hours at room temperature and worked up as described in Example 1.2, and the product was recrystallized from pyridine. Yield: 53%, mp.: 195°–196° C.

Example 5

N-(4-Chlorobenzylideneiminooxycarbonylmethyl)-1,8-naphthalenedicarboximide

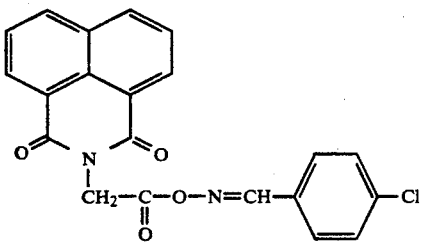

The acyl chloride obtained in stage 1.1 was reacted with 8.6 g (55 mmol) of 4-chlorobenzaldoxime, similarly to Example 1.2, and the product was then recrystallized from pyridine. Yield: 52%, mp.: 204° C.

Example 6 (Compound No. 101)

N,N'-Bis-(hydroxycarbonylmethyl)-1,4,5,8-naphthalenetetracarboxylic acid diimide

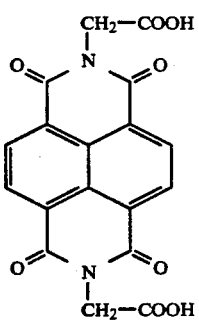

A mixture of 26.8 g (0.1 mol) of 1,4,5,8-naphthalenetetracarboxylic dianhydride, 15.0 g (0.2 mol) of glycerol and 200 ml of dimethylformamide was heated at 140° C for 10 hours, cooled and then poured into 1 l of water in order to precipitate the product. The resulting precipitate was separated off and dried. Yield: 75%, mp.: >300° C.

The compounds of the formula Ia which are listed in Table 1 were synthesized similarly to Examples 1–5 or can be prepared by similar methods Tables 2 and 3 show typical compounds Ib and Ic, respectively.

Examples of syntheses of cyclohexenones of the formula V, where $R^\ominus$ is unsubstituted or substituted butenylphenyl:

Preparation method for Example V.45 from Table B a) 69.1 g (1 mol) of sodium nitrite in 100 ml of water were added to a solution of 93.1 g (1 mol) of aniline in 340 ml of water and 225 ml of concentrated hydrochloric acid at 0° C.

b) 67.6 g (1.25 mol) of gaseous butadiene were passed into 840 ml of acetone and 50 ml of water at −15° C., 15.5 g of copper(II) chloride and 22.5 g of calcium oxide were added and the diazonium salt solution prepared under a) was then added in the course of 2 hours. This reaction mixture was allowed to warm up to 25° C. Stirring was carried out for 6 hours, after which the mixture was extracted with methyl tert-butyl ether, the organic extract was evaporated down and the residue was distilled in a thin film evaporator (0.2 mmHg; 80° C.). This gave a mixture of 1-chloro-4-phenylbut-2-ene and 3-chloro-4-phenylbut-1-ene (78:22) in a total yield of 55%.

c) 78.3 g (0.48 mol) of N-hydroxyphthalimide and 44.2 g 0.32 mol) of potassium carbonate were added in succession to 480 ml of dry N-methylpyrrolidone. 88.8 g (0.54 mol) of the chloride mixture obtained in Example b) were added dropwise at an internal temperature of 40° C. The mixture was heated to 60° C. and stirred for a further 6 hours. It was cooled and then poured onto 2 liters of ice water, and the product was filtered off. Washing and drying gave (E)-N-(4-phenyl-2-butenyloxy)-phthalimide of melting point 70°–71° C. (isopropanol) in a yield of 90% of theory.

d) 11.6 g (0.19 mol) of ethanolamine were added to 55.5 g (0.19 mol) of the phthalimide ester e) in 190 ml of ethyl acetate at 60° C., while stirring. After 5 hours, the precipitated N-hydroxyethylphthalimide was filtered off, and 18.8 g of oxalic acid in 30 ml of ethyl acetate. were added to the filtrate. This gave (E)-4-phenyl-2-butenyloxyamine as the oxalate salt of melting point 127°–129° C. in a yield of 95% of theory.

e) 4.3 g (0.016 mol) of 2-propionyl-5-(3-tetrahydrothiopyranyl)-cyclohexane-1,3-dione, 4.5 g (0.018 mol) of 4-phenylbut-2-enyloxyammonium oxalate and 3.0 g of sodium bicarbonate in 100 ml of methanol was stirred for 16 hours at 25° C. The solvent was distilled off under reduced pressure and the residue was chromatographed over silica gel using a toluene/ethyl acetate mixture in a volume ratio of 8:2.

After removal of the solvent, 2.2 g (34.3% of theory) of 3-hydroxy-2-[1-(4-phenylbut-2-enyloximino)-propyl]-5-(3-tetrahydrothiopyranyl)-cyclohex-2-en-1-one were obtained as a resin.

Unless stated otherwise in Table B, the alkenyl radicals have the E-configuration. The $^1$H-NMR data relate to characteristic selected signals.

Examples of synthesis of cyclohexenones of the formula V, where $R^\ominus$ is unsubstituted or substituted phenyl butyl:

Preparation method for Example V.56 from Table C a) N-(4-(4-Fluorophenyl)-butoxy)-phthalimide 71.5 g (0.23 mol) of N-(4-(4-fluorophenyl)-3-butenyloxy)-phthalimide (prepared according to German Laid-Open Application DOS 3,838,310) were dissolved in 300 ml of tetrahydrofuran, 2 g of palladium on active carbon (10% strength) were added and hydrogenation was carried out under slightly superatmospheric pressure until 1.2 times the theoretical amount of hydrogen had been consumed.

The mixture was filtered under suction over kieselguhr, the filtrate was evaporated down and the residue was recrystallized from isopropanol.

Yield: 62.8 g (87%); mp.: 67°-68° C.

250-MHz-$^1$H-NMR (DMSO-$d_6$)

δ (ppm)=1.8–1.9 (m, 4H); 2.65 (t, 2H); 4.15 (t, 2H); 7.0–7.35 (m, 4H); 7.86 (s, 4H)

b) 61.8 q (0.197 mol) of the phthalimide ether prepared beforehand were introduced a little at a time into 92 ml of ethanolamine. The mixture was heated at 60° C. for 3 hours, cooled and then poured into 400 ml of ice water and extracted three times with 100 ml of dichloromethane. The combined organic phases were washed with saturated sodium chloride solution, dried and evaporated down under reduced pressure.

4-(4-Fluorophenyl)-butoxyamine was isolated as an oil in this manner.

250-MHz-$^1$H-NMR (CDCl$_3$)

δ (ppm)=1.5–1.75 (m, 4H); 2.61 (t, 2H); 3.68 (t, 2H); 5.4 (broad s, 2H); 6.9–7.2 (m, 4H)

c) 2-{1-[4-(4-Fluorophenyl)-butoximino]-propyl}-5-tetrahydrothiopyran-3-yl-3-hydroxycyclohex-2-enone 3 g (1 mmol) of 2-butyryl-3-hydroxy-5-tetrahydrothiopyran-3-ylcyclohex-2-enone were dissolved in 100 ml of dry methanol, and 2.2 g (12 mmol) of 4-(4-fluorophenyl)-butoxyamine were added. The mixture was stirred for 16 hours at room temperature and then evaporated to dryness under reduced pressure. The residue was taken up in diethyl- ether and the solution was chromatographed over silica gel. 3.6 g (80% of theory) of the title compound were obtained.

TABLE 1

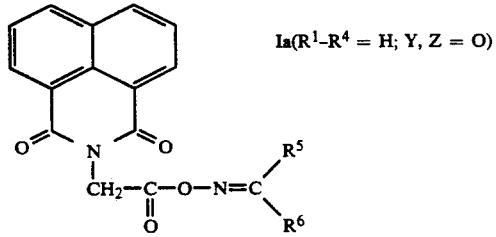

Ia($R^1$–$R^4$ = H; Y, Z = O)

| Example No. | $R^5$ | $R^6$ | mp. [°C.] |
|---|---|---|---|
| 1 | CH$_3$ | CH$_3$ | 107–109 |
| 2 | —CH$_2$—(CH$_2$—)$_3$—CH$_2$— | | 184–185 |
| 3 | CH$_3$ | OC$_2$H$_5$ | 120–125 |
| 4 | H | Phenyl | 195–196 |
| 5 | 4-Cl-Phenyl | H | 204 |
| 6 | CO$_2$CH$_3$ | CH$_3$ | 110–114 |
| 7 | 4-Cl-Phenyl | CH$_3$ | 182–190 |
| 8 | Phenyl | CN | 200–201 |
| 9 | C$_2$H$_5$ | CH$_3$ | |
| 10 | CH$_3$ | i-C$_3$H$_7$ | |
| 11 | n-C$_3$H$_7$ | n-C$_3$H$_7$ | |
| 12 | i-C$_3$H$_7$ | i-C$_3$H$_7$ | |
| 13 | i-C$_4$H$_9$ | i-C$_4$H$_9$ | |
| 14 | CH$_3$ | Neopentyl | |
| 15 | CH$_3$ | —(CH$_2$)$_3$—CH(CH$_3$)$_2$ | |
| 16 | CH$_3$ | —(CH$_2$)$_2$—CH=C(CH$_3$)$_2$ | |
| 17 | CH$_3$ | CH$_2$—OCH$_3$ | |
| 18 | C$_2$H$_5$ | CH$_2$—OCH$_3$ | |
| 19 | 4-Cl-Phenyl | CH$_3$ | |
| 20 | —CH(CH$_3$)—S—CH$_3$ | CH$_3$ | |
| 21 | Benzyl | CH$_3$ | |
| 22 | Phenyl | CH$_3$ | |
| 23 | Phenyl | CH$_2$Cl | |
| 24 | Phenyl | 1,2,4-Triazolylmethyl | |
| 25 | CO—CH$_3$ | CH$_3$ | |
| 26 | CO—CH$_3$ | Phenyl | |
| 27 | 4-N(CH$_3$)$_2$-Phenyl | H | |
| 28 | 4-Cl-Phenyl | H | |
| 29 | 3-Cl-Phenyl | H | |
| 30 | 4-F-Phenyl | H | |
| 31 | 4-CF$_3$-Phenyl | H | |
| 32 | 4-CH$_3$-Phenyl | H | |
| 33 | 4-(CH$_3$—O)-Phenyl | H | |
| 34 | 3-CH$_3$-Phenyl | H | |
| 35 | 3-(CH$_3$—O)-Phenyl | H | |
| 36 | 3-(CHF$_2$—CF$_2$—O)-Phenyl | H | |
| 37 | 4-(CH$_3$—COHN)-Phenyl | H | |
| 38 | 4-CN-Phenyl | H | |
| 39 | 3,4-Cl$_2$-Phenyl | H | |
| 40 | 2,4-Cl$_2$-Phenyl | H | |
| 41 | 2,4-(n-C$_6$H$_{13}$—S)-Phenyl | H | |
| 42 | CH$_3$ | 2-Thienyl | |
| 43 | CH$_3$ | 3-Thienyl | |
| 44 | H | 2-Furyl | |

TABLE 1-continued

Ia (R¹-R⁴ = H; Y, Z = O)

| Example No. | R⁵ | R⁶ | mp. [°C.] |
|---|---|---|---|
| 45 | CH₃ | 2-Furyl | |
| 46 | H | 5,6-Dihydro-Δ³-thiopyran-3-yl | |
| 47 | CH₃ | 5,6-Dihydro-Δ³-pyran-3-yl | |
| 48 | 2-Furyl | n-C₃H₇ | |
| 49 | CH₃ | 2,3-Dihydro-6-CH₃-Δ⁵-pyran-6-yl | |
| 50 | 4-(OH)-3,5-Br₂-Phenyl | H | |
| 51 | 4-(OH)-3,5-I₂-Phenyl | H | |
| 52 | CO—O—C₂H₅ | CN | |
| 53 | —CH₂—(CH₂)₂—CH₂— | | |
| 54 | —CH₂—C(CH₃)₂—CH₂—CH(CH₃)— | | |
| 55 | —CH=C(CH₃)—CH₂—C(CH₃)₂—CH₂— | | |
| 56 | —CH₂—CH(CH₃)—CH₂—CH₂— | | |
| 57 | —CH₂—CH(CH₃)—(CH₂)₂—CH₂— | | |
| 58 | —CH=C(CH₃)—CH₂—CH₂— | | |
| 59 | —CH=CH—(CH₂)₂—CH₂— | | |
| 60 | —CH₂—(CH₂)₄—CH₂— | | |
| 61 | —CH=C(CH₃)—O—C(CH₃)=CH— | | |
| 62 | —CH=C(CH₃)—S—C(CH₃)=CH— | | |
| 63 | —CH₂—CH₂—S—CH₂—CH₂— | | |
| 64 | —CH₂—CH₂—O—CH₂—CH₂— | | |
| 65 | —CH₂—(CH₂)₉—CH₂— | | |
| 66 | 2-methylphenyl-CH₂—CH₂— | | |
| 67 | 2-methylphenyl-CH₂—CH₂—CH₂— | | |
| 68 | —CH₂—(CH₂)₂—CH=C(OC₂H₅)— | | 178–182 |

TABLE 2

Ib (Y, Z = O)

| Example No. | R¹ | R² | R³ | R⁴ | R⁷ | m.p. [°C.] | Reference* |
|---|---|---|---|---|---|---|---|
| 68 | H | H | H | H | CH₂COOH | 270–272 | [1] |
| 69 | H | H | H | H | H | >300 | [2] |
| 70 | H | H | H | H | CH₂COOCH₃ | 175–178 | |
| 71 | H | H | H | H | CH₂COO-i-C₃H₇ | 126 | |
| 72 | H | H | H | H | CH₃ | 210–213 | [3] |
| 73 | H | H | H | H | CH(CH₃)COOH | 251 | [1] |
| 74 | H | H | H | H | CH₂CH₂COOH | 240–243 | [1] |
| 75 | H | H | H | H | 4-(COOH)-Phenyl | >300 | |
| 76 | H | 4-Cl | H | H | CH₂COOH | 265 | [4] |
| 77 | H | 3-NO₂ | H | H | CH₂COOH | 220–222 | [5] |
| 78 | H | H | H | H | n-C₃H₆—COOH | 180–182 | [6] |
| 79 | H | H | H | H | CH₂CONH—OCH₃ | 265–269 | |
| 80 | H | H | H | H | CH₂COO⁻Na⁺ | >300 | [7] |

TABLE 2-continued

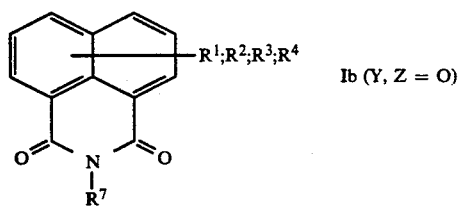

Ib (Y, Z = O)

| Example No. | $R^1$ | $R^2$ | $R^3$ | $R^4$ | $R^7$ | m.p. [°C.] | Reference* |
|---|---|---|---|---|---|---|---|
| 81 | H | H | H | H | $CH_2CON(CH_3)$—$OCH_3$ | | |
| 82 | H | H | H | H | $CH_2COO$-(2,5-dioxo-pyrrolidin-1-yl) | 270–275 | |
| 83 | H | H | H | H | $CH_2SO_3H$ | | |
| 84 | H | H | H | H | $CH_2COO^{\ominus}{}^{\oplus}NH(n-C_4H_9)_3$ | 172 | |
| 85 | H | H | H | H | $CH_2CH_2N(CH_3)_2$ | | |
| 86 | H | 4-$NH_2$ | H | H | H | | |
| 87 | H | 4-$SCH_3$ | H | H | n-$C_4H_9$ | | |
| 88 | H | 4-$SCH_3$ | H | H | n-$C_6H_{13}$ | | |
| 89 | H | 4-$SO_2CH_3$ | H | H | n-$C_4H_9$ | | |
| 90 | 3-Br | 4-NH—$CH_2$—$CH(C_2H_5)$—$C_4H_9$ | H | H | $CH_3$ | | |
| 91 | H | 4-$SCH_2$—COOH | H | H | n-$C_4H_9$ | | |
| 92 | H | H | H | H | $CH_2COO^{\oplus}$ ½ $Ca^{2+}$ | >300 | |
| 93 | 4-Cl | H | H | H | H  OH | 219–226 | |
| 94 | 4-Cl | H | H | H | O—$CH_2CH_3$ | 170–175 | |
| 95 | H | 4-$SCH_2CO_2H$ | H | H | O—$CH_2CH_3$ | 212–220 | |
| 96 | H | 4-$SCH_3$ | H | H | O—$CH_2CH_3$ | 177–182 | |
| 97 | 4-Cl | H | H | H | n-$C_4H_9$ | | |

*The preparation of these compounds is described in the stated literature and in the publications cited there or is carried out by similar methods.

References
[1] A.M. El-Naggar et al., Egypt. J. Chem. 24, 127 (1981);
[2] K.K. Hatzios & P. Zama, Pestic. Sci. 17, 25 (1986);
[3] P.H. Mazzocchi et al., Tterahedron Lett. 29, 513 (1988);
[4] U.S. Pat. No. 4,254,108;
[5] J.J. Ares et al., J. Med. Chem. 29, 2384 (1986);
[6] FR-A-2 521 139;
[7] A.S. Efimov et al., Probl. Endokrinol. 26, 69 (1980).

TABLE 3

Ic ($R^1$; $R^2$ = H)

| Example No. | $R^7$ | m.p. [°C.] Preparation* |
|---|---|---|
| 101 | $CH_2$—COOH | >300 |
| 102 | $CH_2$—$COO^{\ominus}$ $H_3N^{\oplus}(i-C_3H_7)$ | >300 |
| 103 | $CH_2$—$COO^{\ominus}$ $Na^{\oplus}$ | >300 |
| 104 | $CH_2$—CO—$OCH_3$ | >250 |
| 105 | $CH_2$—CO—$OCH(CH_3)_2$ | >250 |

*The preparation of these compounds is described in Example 6 or is carried out by similar methods.

Examples of biological action

The effect of different novel herbicides or herbicide formulations, consisting of the herbicide and the antidote compound, on the growth of desirable and undesirable plants compared with the herbicidal active ingredient alone is demonstrated by the following bio TM logical examples based on greenhouse experiments.

In greenhouse experiments, plastic flower pots having a capacity of about 300 cm³ served as culture vessels and loamy sand containing about 3.0% of humus was used as the substrate. The seeds of the test plants were sown shallowly and separately according to species and were moistened. Thereafter, the pots were covered with transparent plastic covers until the seeds had germinated uniformly and the plants had started growing.

For the postemergence treatment, the test plants were grown to a height of 3–20 cm, depending on the form of growth, before being treated. The herbicides were suspended or emulsified in water as a distributing agent and were sprayed by means of finely distributing nozzles.

The herbicidal cyclohexanone derivatives of the formula V which served as examples were

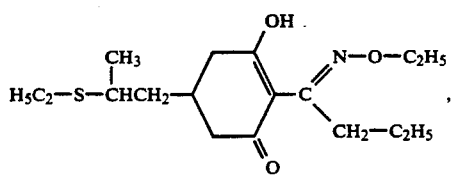

V.2

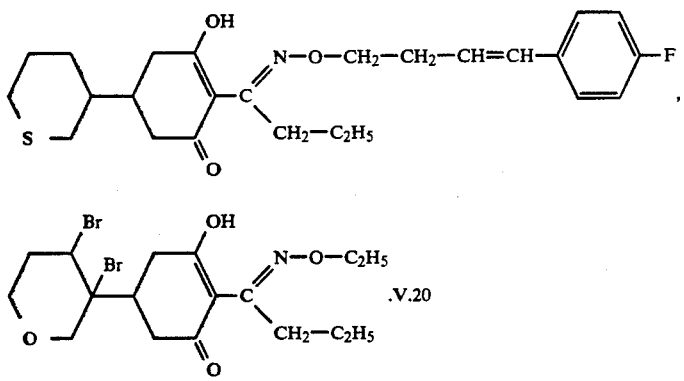

The herbicidal active ingredient V.2 was added in the form of a commercially formulated product (184 g/l of emulsion concentrate) to the preparation of the particular antidote compound and was thus applied together with this compound.

For a comparative experiment, the commercially formulated active ingredient V.2 was applied with a mixture of 80% of cyclohexenone and 20% of Emulphor EL*) (blank formulation, without antidote).
*) ethoxylated castor oil The herbicidal active ingredient V.44 was applied to the plants as a 10% strength by weight solution. The solution was prepared by mixing the active ingredient in a solution of 93% of xylene and 7% of Lutensol ® AP-8**).
 nonionic surfactant based on alkylphenol polyethylene glycol ethers The example herbicide V.20 was applied as a solution which contained 200 g/l in Solvesso 200*).
*** Solvesso ® = particularly pure solvent containing more than 97% by volume of aromatics, for coatings and pesticides For the postemergence treatment, all antidote compounds were prepared in a mixture consisting of 80% of cyclohexenone and 20% of Emulphor EL, with 10% by weight of active ingredient.

List of test plants

| Botanical name | Common name |
| --- | --- |
| Alopecurus myosuroides | blackgrass |
| Lolium multiflorum | annual ryegrass |
| Triticum aestivum | wheat |
| Setaria italica | foxtail millet |
| Zea mays | Indian corn |

The test vessels were placed in a greenhouse, from 18° to 30° C. being preferred for heat-loving species and from 10° to 25° C. being preferred for species of more temperate climates.

For open air experiments, a trial field was divided into small plots of 2 m², and the test plants were sowed in rows. The soil of the field consisted of loamy sand containing about 1.5% of humus and had a pH of 6. The agents were suspended in water as a carrier and distributing agent, and the plants were sprayed to run-off with said agents by the postemergence method using a mobile spray booth which had finely distributing nozzles.

The experimental period was from 3 to 4 weeks. During this time, the plants were tended and their reaction to the individual treatments was recorded.

The damage caused by the chemical agents was evaluated on the basis of a scale from 0 to 100% in comparison with the untreated control plants. 0 means no damage and 100 means complete destruction of the plants.

The Tables below document the antidote action of the novel compounds of Example Nos. 68, 86, 87, 88 and 89.

These compounds of said Examples substantially improve the toleration of the herbicide V.2 by crops. In the open air, the compound of Example No. 68 substantially improves the toleration of the herbicide V.6 by corn and in particular the toleration of the herbicide V.20 by wheat.

TABLE 1

Improvement of the toleration of the herbicide V.2 by wheat as a result of admixing an antidote compound from the Examples and effecting application by the postemergence method; greenhouse experiment

| | | | Test plants and damage % | | |
| --- | --- | --- | --- | --- | --- |
| Herbicide No. | Antidote No. | Application rate kg/ha a.i. | Crop Triticum aestivum* | Undesirable plant Lolium multif. | Setaria italica |
| V.2 | — | 0.03 | 70 | 98 | — |
| V.2 | 68 | 0.03 + 0.125 | 10 | 95 | — |
| V.2 | 87 | 0.03 + 0.125 | 10 | 95 | — |
| V.2 | 89 | 0.02 + 0.125 | 10 | 95 | — |
| V.2 | — | 0.015 | 40 | — | 100 |
| V.2 | 86 | 0.015 + 0.06 | 20 | — | 100 |

*Variety: Okapi

TABLE 2

Improvement of the toleration of herbicide No. V.20 by wheat on postemergence application by admixing an antidote compound from the Examples; open air experiment

| | | | Test plants and damage % | |
| --- | --- | --- | --- | --- |
| Herbicide No. | Antidote No. | Application rate kg/ha a.i. | Crop Triticum aestivum* | Undesirable plant Alopecurus myosuroides |
| V.20 | — | 0.5 | 35 | 95 |
| V.20 | 68 | 0.5 + 1.0 | 2 | 90 |

*Variety: Okapi

TABLE 3

Improvement of the toleration of herbicide No. V.2 by corn on postemergence application by admixing an antidote compound from the Examples; greenhouse experiment

| | | | Test plants and damage % | |
| --- | --- | --- | --- | --- |
| Herbicide No. | Antidote No. | Application rate kg/ha a.i. | Crop Zea mays* | Undesirable plant Setaria italia |
| V.2 | — | 0.015 | 85 | 95 |
| V.2 | 88 | 0.015 + 0.06 | 20 | 95 |

*Variety: Mutin

TABLE 4

Improvement of the toleration of herbicide No. V.6 by corn on postemergence application by admixing an antidote compound from the Examples; open air experiment

| Herbicide No. | Antidote No. | Application rate kg/ha a.i. | Test plants and damage % | |
|---|---|---|---|---|
| | | | Crop Zea mays* | Undesirable plant Setaria italia |
| V.44** | — | 0.5 | 58 | 100 |
| V.44** | 68 | 0.5 + 0.25 | 15 | 100 |

*Variety: Mutin
**1 l/ha of wetting agent was also applied with the active ingredient formulation.

We claim:
1. A substituted 1,8-naphthalenedicarboximide of the formula Ia

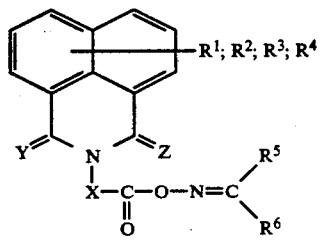

where
$R^1$ to $R^4$ are each hydrogen, halogen, hydroxyl, mercapto, cyano, thiocyanato, nitro, $C_1-C_6$-alkyl may be unsubstituted or partially or completely halogenated, $C_2-C_6$-alkenyl, $C_2-C_6$-alkynyl, $C_3-C_8$-cycloalkyl, $C_3-C_8$-cycloalkoxy, amino, $C_1-C_8$-alkylamino, di-($C_1-C_6$-alkylamino), amino-$C_1-C_4$-alkyl, $C_1-C_6$-alkylamino-$C_1-C_6$-alkyl, di-$C_1-C_6$-alkylamino-$C_1-C_4$-alkyl, $C_1-C_4$-alkoxy, $C_1-C_4$-alkylthio, $C_1-C_4$-alkoxy-$C_1-C_4$-alkyl, $C_1-C_4$-alkylthio-$C_1-C_4$-alkyl, $C_1-C_6$-alkylcarbonyl, $C_1-C_6$-alkylcarbonyloxy, $C_1-C_6$-alkoxycarbonyl, hydroxycarbonyl, hydroxycarbonyl-$C_1-C_4$-alkyl, hydroxycarbonyl-$C_1-C_4$-alkoxy, hydroxycarbonyl-$C_1-C_4$-alkylthio, hydroxysulfonyl, $C_1-C_6$-alkylsulfinyl, $C_1-C_6$-alkylsulfonyl, $C_1-C_4$-alkoxysulfonyl, aminosulfonyl, $C_1-C_4$-alkylaminosulfonyl, di-$C_1-C_4$-alkylaminosulfonyl, hydrazino which may carry not more than three $C_1-C_4$-alkyl radicals, phenyl, phenyl-$C_1-C_3$-alkyl, naphthyl, naphthyl-$C_1-C_3$-alkyl, 2-pyrrolyl, 2-thienyl, 3-furanyl, 2-pyridyl, phenoxycarbonyl, naphthyloxycarbonyl, phenylcarbonyl, naphthylcarbonyl,phenylcarbonyloxy,naphthylcarbonyloxy, phenyl-$C_1-C_3$-alkoxy, naphthyl-$C_1-C_3$-alkoxy, a 5-membered or 6-membered hetaryl-$C_1-C_3$-alkoxy group, phenylsulfinyl, naphthylsulfinyl, phenylsulfonyl, naphthylsulfonyl, phenoxysulfonyl, naphthyloxysulfonyl, where the aryl and hetaryl moieties of the stated substituents may furthermore carry not more than three of the following substituents: halogen, cyano, nitro, $C_1-C_4$-alkyl, $C_1-C_4$-alkoxy, amino, $C_1-C_6$-alkylamino, di-$C_1-C_6$-alkylamino or partially or completely halogenated $C_1-C_4$-alkyl;
X is a $C_1-C_6$-alkylene chain which may furthermore carry one of the following radicals: halogen, hydroxyl, di-$C_1-C_4$-alkylamino, $C_1-C_4$-alkoxycarbonyl, cyano, $C_1-C_6$-alkylcarbonyl, $C_1-C_6$-alkylcarbonyloxy, phenyl, naphthyl, 5-membered or 6-membered hetaryl, phenyl-$C_1-C_3$-alkyl, naphthyl-$C_1-C_3$-alkyl or 5-membered or 6-membered hetaryl-$C_1-C_3$-alkyl, where the aryl and hetaryl moieties of the six last-mentioned radicals may furthermore carry not more than 3 halogen atoms or $C_1-C_4$-alkyl groups;
$R^5$ is hydrogen, cyano, $C_1-C_6$-alkyl, $C_2-C_6$-alkenyl, $C_1-C_4$-alkoxy-$C_1-C_4$-alkyl, $C_1-C_4$-alkylthio-$C_1-C_4$-alkyl, $C_1-C_4$-alkoxycarbonyl, acetyl, $C_3-C_6$-cycloalkyl, benzoyl, naphthoyl, 5-membered or 6-membered hetaroyl group, phenyl, naphthyl, phenyl-$C_1-C_3$-alkyl, naphthyl-$C_1-C_3$-alkyl or a 5-membered or a 6-membered hetaryl or hetaryl-$C_1-C_3$-alkyl group, where the aryl and hetaryl moieties of the six last-mentioned groups may furthermore carry not more than three of the following radicals: halogen, hydroxyl, cyano, trifluoromethyl, $C_1-C_6$-alkoxy which may be unsubstituted or partially or completely halogenated, $C_1-C_6$-alkylthio, $C_1-C_6$-alkyl, di-$C_1-C_3$-alkylamino or acetylamino;
$R^6$ is hydrogen, cyano, $C_1-C_6$-alkyl which may be unsubstituted or partially or completely halogenated, $C_1-C_4$-alkoxy, $C_1-C_4$-alkoxy-$C_1-C_4$-alkyl, diazolylmethyl, triazolylmethyl, $C_1-C_6$-alkoxycarbonyl, furyl, tetrahydrofuryl, thienyl, dihydropyranyl, dihydrothiopyranyl, tetrahydropyranyl or tetrahydrothiopyranyl or phenyl if $R^5$ is hydrogen, methyl or acetyl, or together with $R^5$ and the common carbon atom, may form a $C_3-C_{12}$-cycloalkyl or 4-oxocyclohexadienyl radical or a 5-membered or 6-membered ring which may be saturated or partially or completely unsaturated, may contain an oxygen or sulfur atom as a hetero atom and may furthermore carry not more than three $C_1-C_3$-alkyl groups or a fused-on benzene ring, and Y and Z are each oxygen or sulfur, with the proviso that $R^5$ and $R^6$ are not simultaneously hydrogen, and the plant-tolerated salt thereof in which $R^1$, $R^2$, $R^3$ and $R^4$ are each hydroxycarbonyl, hydroxycarbonyl-$C_1-C_4$-alkyl, hydroxycarbonyl-$C_1-C_4$-alkoxy, hydroxycarbonyl-$C_1-C_4$-alkylthio or hydroxysulfonyl.

2. A herbicidal composition containing a herbicidally effective amount of one or more substituted 1,8-naphthalenedicarboximides of the formula Ia

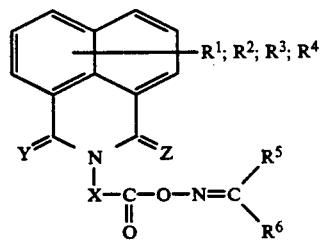

where
$R^1$ ro $R^4$ are each hydrogen, halogen, hydroxyl, mercapto, cyano, thiocyanato, nitro, $C_1-C_6$-alkyl which may be unsubstituted or partially or completely halogenated, $C_2-C_6$-alkenyl, $C_2-C_6$-alkynyl, $C_3-C_8$-cycloalkyl, $C_3-C_8$-cycloalkoxy, amino, $C_1-C_8$-alkylamino, di-($C_1-C_6$-alkylamino), amino-$C_1-C_4$-alkyl, $C_1-C_6$-alkylamino-$C_1-C_4$-alkyl, di-$C_1-C_6$-alkylamino-$C_1-C_4$-alkyl, $C_1-C_4$-alkoxy, $C_1-C_4$-alkylthio, $C_1-C_4$-alkoxy-$C_1-C_4$-alkyl, $C_1-C_4$-alkylthio-$C_1-C_4$-alkyl, $C_1-C_6$-alkylcarbonyl, $C_1-C_6$-alkylcarbonyloxy, $C_1-C_6$-alkoxycarbonyl, hydroxycarbonyl, hydroxycarbonyl-$C_1-C_4$-alkyl, hydroxycarbonyl-$C_1-C_4$-alkoxy, hydroxycarbonyl-$C_1-C_4$-alkylthio, hydroxysulfonyl, $C_1-C_6$-alkylsulfinyl, $C_1-C_6$-alkylsulfonyl, $C_1-C_4$-alkoxysulfonyl, aminosulfonyl, $C_1-C_4$-alkylaminosulfonyl, di-$C_1-C_4$-alkylaminosulfonyl, hydrazino which may carry not more than three $C_1-C_4$-alkyl radicals, phenyl, phenyl-$C_1-C_3$-alkyl, naphthyl, naphthyl-$C_1-C_3$-alkyl, 2-pyrrolyl, 2-thienyl, 3-furanyl, 2-pyridyl, phenoxy, naphthyloxy, phenylthio, naphthylthio, phenoxycarbonyl, naphthyloxycarbonyl, phenylcarbonyl, naphthylcarbonyl, phenylcarbonyloxy, naphthylcarbonyloxy, phenyl-$C_1-C_3$-alkoxy, naphthyl-$C_1-C_3$-alkoxy, phenylsulfinyl, naphthylsulfinyl, phenylsulfonyl, naphthylsulfonyl, where the aryl or hetaryl moieties of the stated substituents may furthermore carry not more than three of the following substituents: halogen, cyano, nitro, $C_1-C_4$-alkyl, $C_1-C_4$-alkoxy, amino, $C_1-C_6$-alkylamino, di-$C_1-C_6$-alkylamino or partially or completely halogenated $C_1-C_6$-alkyl;

X is a $C_1-C_6$-alkylene chain which may furthermore carry one of the following radicals: halogen, hydroxyl, mercapto, $C_1-C_4$-alkyl, $C_1-C_4$-alkoxy, $C_1-C_4$-alkylthio, di-$C_1-C_4$-alkylamino, $C_1-C_4$-alkoxycarbonyl, cyano, $C_1-C_6$-alkylcarbonyl, $C_1-C_6$-alkylcarbonyloxy, phenyl, naphthyl, 2-pyrroyl, 2-thienyl, 3-furanyl, 2-pyridyl, phenyl-$C_1-C_3$-alkyl, naphthyl-$C_1-C_3$-alkyl where the aryl and hetaryl moieties may furthermore carry not more than 3 halogen atoms or $C_1-C_4$-alkyl groups;

$R^5$ is hydrogen, cyano, $C_1-C_6$-alkyl, $C_2-C_6$-alkenyl, $C_1-C_4$-alkoxy-alkyl, $C_1-C_4$-alkylthio-$C_1-C_4$-alkyl, $C_1-C_4$-alkoxycarbonyl, acetyl, $C_3-C_6$-cycloalkyl, benzoyl, naphthoyl, pyrodylcarbonyl, thienylcarbonyl phenyl, naphthyl, phenyl-$C_1-C_3$-alkyl, naphthyl-$C_1-C_3$-alkyl, where the aryl and hetaryl moieties may furthermore carry not more than three of the following radicals: halogen, hydroxyl, cyano, trifluoromethyl, $C_1-C_6$-alkoxy which may be unsubstituted or partially or completely halogenated, $C_1-C_6$-alkylthio, $C_1-C_6$-alkyl, di-$C_1-C_3$-alkylamino or acetylamino;

$R^6$ is hydrogen, cyano, $C_1-C_6$-alkyl which may be unsubstituted or partially or completely halogenated, $C_1-C_4$-alkoxy, $C_1-C_4$-alkoxy-$C_1-C_4$-alkyl, diazolylmethyl, triazolylmethyl, $C_1-C_6$-alkoxycarbonyl, furyl, tetrahydrofuryl, thienyl, dihydropyranyl, dihydrothiopyranyl, tetrahydropyranyl or tetrahydrothiopyranyl or phenyl if $R^5$ is hydrogen, methyl or acetyl, or together with $R^5$ and the common carbon atom, may form a $C_3-C_{12}$-cycloalkyl or 4-oxocyclohexadienyl radical or a 5-membered or 6-membered ring which may be saturated or partially or completely unsaturated, may contain an oxygen or sulfur atom as a hetero atom and may furthermore carry not more than three $C_1-C_3$-alkyl groups or a fused-on benzene ring, and Y and Z are each oxygen or sulfur, with the proviso that $R^5$ and $R^6$ are not simultaneously hydrogen, or a plant-tolerated salt thereof in which $R^1$, $R^2$, $R^3$ and $R^4$ are each hydroxycarbonyl, hydroxycarbonyl-$C_1-C_4$-alkyl, hydroxycarbonyl-$C_1-C_4$-alkoxy, hydroxycarbonyl-$C_1-C_4$-alkylthio or hydroxysulfonyl, and/or one or more 1,8-napthalenedicarboximides of the formula Ib

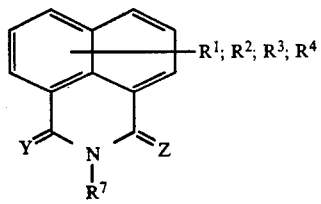

Ib where $R^1$, $R^2$, $R^3$ and $R^4$ are defined as set forth above in connection with formula Ia and
where $R^7$ is a) hydrogen, hydroxyl, cyano, $C_1-C_6$-alkyl, which may be unsubstituted or partially or completely halogenated, $C_1-C_6$-hydroxyalkyl, $C_2-C_6$-alkenyl, $C_1-C_4$-alkoxy, $C_1-C_4$-alkoxy-$C_1-C_4$-alkyl, $C_1-C_4$-alkylthio-$C_1-C_4$-alkyl, amino, $C_1-C_4$-alkylamino, di-$C_1-C_4$-alkylamino, $C_3-C_8$-cycloalkyl, $C_3-C_8$-cycloalkoxy, acyl, $C_1-C_4$-alkoxy-carbonyl-$C_1-C_6$-alkyl, aminocarbonyl-$C_1-C_6$-alkyl, $C_1-C_4$-alkyl, $C_1-C_4$-alkoxyaminocarbonyl-$C_1-C_6$-alkyl, di-$C_1-C_4$-alkyl-aminocarbonyl-$C_1-C_6$-alkyl, $C_1-C_4$-alkyl, $C_1-C_4$-alkoxyaminocarbonyl-$C_1-C_6$-alkyl, N-($C_1-C_4$-alkoxy)-N-($C_1-C_4$)-aminocarbonyl-$C_1-C_6$-alkyl, $C_1-C_4$-alkylthiocarbonyl-$C_1-C_6$-alkyl, $C_1-C_4$-alkoxycarbonyl, $C_1-C_4$-alkylcarbonyloxy, $C_1-C_4$-alkoxysulfonyl-$C_1-C_6$-alkyl, aminosulfonyl-$C_1 6 C_4$-alkyl, $C_1-C_4$-alkylaminosulfonyl-$C_1-C_6$-alkyl or di-$C_1-C_4$-alkylaminosulfonyl-$C_1-C_6$-alkyl, or b) hydroxycarbonyl-$C_1-C_6$-alkyl, hydroxycarbonyl-$C_1-C_6$-alkoxy or hydroxysulfonyl-$C_1-C_6$-alkyl, or c) phenyl, naphthyl, 2-pyrroyl, 2-thienyl, 3-furanyl, 2-pyridyl, phenyl-$C_1-C_4$-alkyl, naphthyl-$C_1-C_4$-alkyl, phenoxy, naphthyloxy, phenyl-$C_1-C_4$-alkoxy, naphthyl-$C_1-C_4$-alkoxy, benzoyl, naphthoyl, phenoxycarbonyl-$C_1-C_6$-alkyl, naphthyloxycarbonyl-$C_1-C_6$-alkyl where the aryl and hetaryl moieties of the stated substituents may furthermore carry not more than 3 halogen atoms or $C_1-C_4$-alkyl groups or one of the following radicals: hydroxycarbonyl, nitro, cyano, amino, $C_1-C_4$-alkylamino, di-$C_1-C_4$-alkylamino, $C_1-C_4$-alkoxy or partially or completely halogenated $C_1-C_4$-alkyl, or d) a group

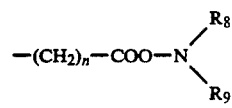

where n is an integer from 1 to 6 and $R^8$ and $R^9$ are each $C_1-C_3$-alkyl or $C_1-C_3$-alkycarbonyl, where $R^8$ and $R^9$, together with the common nitrogen atom, may furthermore form a 5-membered or 6-membered ring, and/or a 1,8-naphthalenedicarboximide of the formula Ic

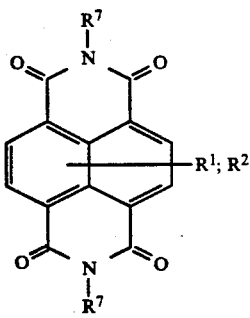

or a plant-tolerated salt of the compounds Ib and-/or Ic in which $R^1$, $R^2$, $R^3$ and $R^4$ are each hydroxycarbonyl, hydroxycarbonyl-$C_1$-$C_4$-alkyl, hydroxycarbonyl-$C_1$-$C_4$-alkoxy, hydroxycarbonyl-$C_1$-$C_4$-alkylthio or hydroxysulfonyl and/or $R^7$ is hydrocarbonyl-$C_1$-$C_6$-alkyl, hydroxycarbonyl-$C_1$-$C_6$-alkoxy or hydroxysulfonyl-$C_1$-$C_6$-alkyl, and one or more herbicidal active ingredients from the group consisting of A) the 2-(4-hetaryloxy)-or 2-)4-aryloxy-phenoxyacetic acid derivatives of the formula IV

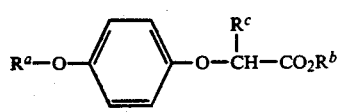

where
$R^a$ is phenyl, pyridyl, benzoxazyl, benzothiazolyl or benzopyrazinyl, where these aromatic ring systems may carry not more than two of the following radicals: hydrogen, nitro, $C_1$-$C_4$-alkyl, $C_1$-$C_4$-haloalkyl and/or $C_1$-$C_4$-haloalkoxy;
$R^b$ is hydrogen, $C_1$-$C_5$-alkyl $C_3$-$C_5$-alkylideneimino, $C_3$-$C_5$-alkylideneiminoxy-$C^2$- or -$C_3$-alkyl or one equivalent of a plant-tolerated cation and
$R^c$ is hydrogen or methyl, or
B) the cyclohexenone derivatives of the formula V

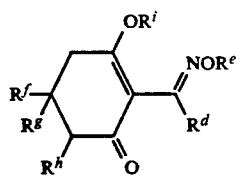

where
$R^d$ is $C_1$-$C_4$-alkyl;
$R^e$ is $C_1$-$C_4$-alkyl, $C_3$- or $C_4$-alkenyl, $C_3$- or $C_4$-alkynyl or $C_3$- or $C_4$-haloalkenyl;
$C_1$-$C_4$-alkylphenyl or $C_1$-$C_4$-alkenylphenyl, where the alkyl and alkenyl moieties may furthermore carry not more than 3 $C_1$-$C_3$-alkyl groups and/or halogen atoms and the phenyl moiety may carry not more than 5 halogen atoms or a benzyloxycarbonyl or phenyl radical and/or not more than 3 of the following substituents: nitro, cyano, $C_1$-$C_4$-alkyl, $C_1$-$C_4$-alkoxy, $C_1$-$C_4$-alkylthio, partially or completely halogenated $C_1$-$C_4$-alkyl, partially or completely halogenated $C_1$-$C_4$-alkoxy, carboxyl or $C_1$-$C_4$-alkoxycarbonyl; thienyl which may furthermore carry a halogen atom; $R^f$ is $C_1$-$C_4$-alkyl which may be monosubstituted by $C_1$-$C_4$-alkylthio or by $C_1$-$C_4$-alkoxy;

a 5-member or 6-membered saturated or monounsaturated ring system which, in addition to carbon members, may contain an oxygen or sulfur atom or a sulfoxyl or sulfonyl group, where this ring may carry not more than three of the following radicals: hydroxyl, halogen, $C_1$-$C_4$-alkyl, $C_1$-$C_4$-haloalkyl, $C_1$-$C_4$-alkoxy and/or $C_1$-$C_4$-alkylthio;

phenyl or pyridyl where these groups may carry not more than three of the following radicals: $C_1$-$C_4$-alkyl, $C_1$-$C_4$-haloalkyl, $C_1$-$C_4$-alkoxy, $C_1$-$C_4$-alkylthio, $C_3$-$C_6$-alkenyloxy, $C_1$-$C_4$-alkoxy-$C_1$-$C_3$-alkyl, $C_1$-$C_4$-alkoxy-$C_1$-$C_4$-dialkoxy-$C_1$-$C_3$-alkyl, formyl, halogen and/or benzoylamino, or pyrrolyl, pyrazolyl, thiazolyl or isoxazolyl, each of which may furthermore carry a $C_1$-$C_4$-alkyl group;

$R^g$ is hydrogen, hydroxyl or, if $R^f$ is $C_1$-$C_6$-alkyl, $C_1$-$C_6$-alkyl, $R^h$ is hydrogen, cyano, halogen, $C_1$-$C_4$-alkoxycarbonyl or a group

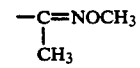

and
$R^r$ is hydrogene or one equivalent of an environmentally compatible cation.

3. A herbicidal composition as defined in claim 2, containing a substitute 1,8-naphthalenedicarboximide Ia and/or Ib and/or Ic and a herbicide IV or a herbicide V in a weight ratio of 0.01:1 to 10:1.

4. A method for selectively controlling undesirable plant growth, wherein a substituted 1,8-naphthalenedicarboximide Ia and/or Ib and/or Ic and A) a 2-(4-hetaryloxy)- or 2-(4-aryloxy)-phenoxyacetic acid derivative of the formula IV or B) a cyclohexenone derivative of the formula V as claimed in claim 2 are applied simultaneously or in succession, before, during or after sowing of the crops, before or during emergence of the crops.

5. A method for selectively controlling undesirable plant growth, wherein the leaves of the crops and of the undesirable plants are treated by the postemergence method, simultaneously or in succession with a substituted 1,8-naphthalenedicarboximide Ia and/or Ib and/or Ic and A) with a 2-(4-hetaryloxy)- or 2-(4-aryloxy)-phenoxyacetic acid derivative of the formula IV or B) with a cyclohexenone derivative of the formula V as claimed in claim 2.

6. A method for preventing damage to crops by herbicidal 2-(4-hetaryloxy)- or 2-(4-aryloxy)-phenoxyacetic acid derivatives of the formula IV or by herbicidal cyclohexenone derivatives of the formula V as claimed in claim 2, wherein the seed of the crops is treated with an amount, having an antagonistic effect, of a substituted 1,8-naphthalenedicarboximide of the formula Ia and/or Ib and/or Ic as claimed in claim 2.

7. A method as claimed in claim 4, wherein the crops are barley, wheat, corn, millet and rice.

8. A method as claimed in claim 5, wherein the crops are barley, wheat, corn, millet and rice.

9. A method as claimed in claim 6, wherein the crops are barley, wheat, corn, millet and rice.

* * * * *

UNITED STATES PATENT AND TRADEMARK OFFICE
CERTIFICATE OF CORRECTION

PATENT NO. : 5,076,831

DATED : December 31, 1991

INVENTOR(S) : SAUPE et al.

It is certified that error appears in the above-identified patent and that said Letters Patent is hereby corrected as shown below:

Column 41, Line 30: That part reading "$C_1$-$C_6$-alkyl may" should read --$C_1$-$C_6$-alkyl which may --

Column 41, Line 49: After "2-pyridyl," please insert --phenoxy, naphthyloxy, phenylthio, naphthylthio, --

Column 41, Line 64: After "hydroxyl," please insert --mercapto, $C_1$-$C_4$-alkyl, $C_1$-$C_4$-alkoxy, $C_1$-$C_4$-alkylthio, --

Column 42, Line 38: Please delete "and the" and insert therefor --or a --

Column 43, Line 17: After "naphthylsulfonyl," please insert --phenoxysulphonyl, naphthyloxysulfonyl,--

Column 43, Line 23: That part reading "$C_1$-$C_6$-alkyl"" should read --$C_1$-$C_4$-alkyl;--

Column 43, Line 38: That part reading "pyrodyl-" should read --pyridyl- --

Column 44, Line 24: That part reading "$C_1$-$C_4$-alkyl,$C_1$ - $C_4$ alkoxyaminocar- should read--$C_1$ - $C_4$ alkylaminocarbonyl-$C_1$ -$C_6$alkyl, Column 45, Line 20: That part reading "hydrocarbonyl-$C_1$-$C_6$-alkyl," should read -- hydroxycarbonyl-$C_1$-$C_6$-alkyl, --

UNITED STATES PATENT AND TRADEMARK OFFICE
CERTIFICATE OF CORRECTION

PATENT NO. : 5,076,831
DATED : December 31, 1991
INVENTOR(S) : Saupe, et. al.

It is certified that error appears in the above-indentified patent and that said Letters Patent is hereby corrected as shown below:

Column 46, Line 31: That part reading "substitute" should read --substituted--

Signed and Sealed this

Fifteenth Day of June, 1993

Attest:

MICHAEL K. KIRK

Attesting Officer

Acting Commissioner of Patents and Trademarks